US009285322B2

(12) United States Patent
Cremer

(10) Patent No.: US 9,285,322 B2
(45) Date of Patent: *Mar. 15, 2016

(54) PH MODULATION METHODS AND SYSTEMS FOR DETECTING BINDING EVENTS

(75) Inventor: Paul S. Cremer, College Station, TX (US)

(73) Assignee: The Texas A&M University System, College Station, TX (US)

( * ) Notice: Subject to any disclaimer, the term of this patent is extended or adjusted under 35 U.S.C. 154(b) by 935 days.

This patent is subject to a terminal disclaimer.

(21) Appl. No.: 13/309,313

(22) Filed: Dec. 1, 2011

(65) Prior Publication Data

US 2012/0142021 A1    Jun. 7, 2012

Related U.S. Application Data

(60) Provisional application No. 61/418,706, filed on Dec. 1, 2010.

(51) Int. Cl.
| | |
|---|---|
| G01N 31/00 | (2006.01) |
| G01N 33/53 | (2006.01) |
| G01N 21/77 | (2006.01) |
| C07D 471/06 | (2006.01) |
| G01N 33/58 | (2006.01) |
| G01N 33/543 | (2006.01) |
| G01N 33/84 | (2006.01) |
| B82Y 30/00 | (2011.01) |

(52) U.S. Cl.
CPC ............. *G01N 21/77* (2013.01); *C07D 471/06* (2013.01); *G01N 33/54366* (2013.01); *G01N 33/582* (2013.01); *G01N 33/84* (2013.01); *B82Y 30/00* (2013.01); *G01N 2021/7786* (2013.01)

(58) Field of Classification Search
CPC ...... G01N 21/64; C07D 471/06; A63C 5/075; A63C 9/00; B82Y 30/00
See application file for complete search history.

(56) References Cited

U.S. PATENT DOCUMENTS

| | | | |
|---|---|---|---|
| 5,798,276 A | 8/1998 | Haugland | |
| 5,955,612 A | 9/1999 | Ahlem | |
| 6,562,632 B1 | 5/2003 | Szalecki | |
| 7,056,653 B2 | 6/2006 | Barenholz | |
| 7,514,267 B1 | 4/2009 | Lopez | |
| 8,815,778 B2* | 8/2014 | Jung et al. ......................... 506/9 |
| 2002/0039728 A1* | 4/2002 | Kain et al. ......................... 435/6 |
| 2002/0177144 A1 | 11/2002 | Remacle | |
| 2003/0099950 A1 | 5/2003 | Hanna | |
| 2005/0233332 A1 | 10/2005 | Collis | |
| 2008/0213133 A1 | 9/2008 | Wallace | |
| 2008/0248492 A1 | 10/2008 | Yamazaki | |
| 2012/0028823 A1 | 2/2012 | Jung | |

FOREIGN PATENT DOCUMENTS

WO    2010/080640 A2    7/2010

OTHER PUBLICATIONS

Hansen et al. (Journal of Immunological Methods, vol. 203, 1997, pp. 199-207).*
Hansen et al. (Journal of Immunological Methods, 203, 1997, pp. 199-207).*
Hansen, M.H., et al., "Detection of PNA/DNA Hybrid Molecules by Antibody Fab Fragments Isolated From a Phage Display," Journal of Immunological Methods 203(2):199-207, Apr. 1997.
International Search Report and Written Opinion mailed Jul. 20, 2012, issued in corresponding International Application No. PCT/US2011/062926, filed Dec. 1, 2011, 8 pages.
International Preliminary Report on Patentability mailed Jun. 4, 2013, issued in corresponding International Application No. PCT/US2011/062926, filed Dec. 1, 2011, 6 pages.
Jung, H., et al., "Detecting Protein-Ligand Binding on Supported Bilayers by Local pH Modulation," Journal of the American Chemical Society 131(3):1006-1014, Jan. 2009. (Author Manuscript provided, PMCID: PMC3195364, available in PMC Oct. 17, 2011, 23 pages).
Liu, J., et al., "PNA-DNA Hybridization Study Using Labeled Streptavidin by Voltammetry and Surface Plasmon Fluorescence Spectroscopy," Analytical Chemistry 78(2):470-476, Jan. 2006.
Nikiforov, T.T., and S. Jeong, "Detection of Hybrid Formation Between Peptide Nucleic Acids and DNA by Fluorescence Polarization in the Presence of Polylysine," Analytical Biochemistry 275(2):248-253, Nov. 1999.
Corrie, J.E.T., et al., "Chemistry of Sulforhodamine-Amine Conjugates," Bioconjugate Chemistry 12(2):186-194, Mar. 2001.
Daniel, S., et al., "Separation of Membrane-Bound Compounds by Solid-Supported Bilayer Electrophoresis," J. Am. Chem. Soc. 129(26), 8072-8073, Jul. 2007.
Fears, K.P., et al., "Determination of the Surface pK of Carboxylic- and Amine-Terminated Alkanethiols Using Surface Plasmon Resonance Spectroscopy," Langmuir 24(3):837-843, Feb. 2008.
Fromherz, P., "Lipid Coumarin Dye as a Probe of Interfacial Electrical Potential in Biomembranes," in S. Fleischer and B. Fleischer (eds.), "Methods in Enzymology," vol. 171, Academic Press, Inc., San Diego, 1989, pp. 376-387.
Marchesini, S., et al., "Novel Fluorescent pH Indicator for the Acidic Range," Biochemistry International 27(3):545-550, Jul. 1992.
Sapuri, A.R., et al., "Electrostatically Targeted Intermembrane Lipid Exchange With Micropatterned Supported Membranes," Langmuir 19(5):1606-1610, Mar. 2003.
International Search Report and Written Opinion mailed Sep. 30, 2010, issued in International Application No. PCT/US2009/068854, filed Dec. 18, 2009, 8 pages.
Chamoun-Emanuelli, A.M., et al., "Phenothiazines Inhibit Hepatitis C Virus Entry, Likely by Increasing the Fluidity of Cholesterol-Rich Membranes," Antimicrobial Agents and Chemotherapy 57(6):2571-2581, Jun. 2013.

(Continued)

*Primary Examiner* — Lisa Cook
(74) *Attorney, Agent, or Firm* — Christensen O'Connor Johnson Kindness PLLC

(57) ABSTRACT

Methods and systems for detecting binding between first and second molecules using a pH-sensitive fluorophore. A change in fluorescence emission intensity of the fluorophore is indicative of binding.

26 Claims, 12 Drawing Sheets

(56) References Cited

OTHER PUBLICATIONS

Eggeling, C., et al., "Photobleaching of Fluorescent Dyes Under Conditions Used for Single-Molecule Detection: Evidence of Two-Step Photolysis," Analytical Chemistry 70(13):2651-2659, Jul. 1998.

Huang, D., et al., "Monitoring Protein-Small Molecule Interactions by Local pH Modulation," Biosensors and Bioelectronics 38(1):74-78, Oct.-Dec. 2012.

Huang, D., et al., "Sensing Small Molecule Interactions with Lipid Membranes by Local pH Modulation," Analytical Chemistry 85(21):10240-10248, Nov. 2013.

Robison, A.D., et al., "Fluorescence Modulation Sensing of Positively and Negatively Charged Proteins on Lipid Bilayers," Biointerphases 8(1):Dec. 1, 2013, 9 pages.

* cited by examiner

PH MODULATION METHODS AND SYSTEMS FOR DETECTING BINDING EVENTS

CROSS-REFERENCE TO RELATED APPLICATION

This application claims the benefit of U.S. Provisional Patent Application No. 61/418,706, filed Dec. 1, 2010, expressly incorporated herein by reference in its entirety.

STATEMENT OF GOVERNMENT LICENSE RIGHTS

This invention was made with Government support under Grant No. N00014-08-1-0467 awarded by the Office of Naval Research, Grant No. R01 GM070622 awarded by the National Institutes of Health, and Grant No. W911NF-05-1-0494 awarded by the Army Research Office. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 38325_Seq.txt. The text file is 13.9 KB; was created on Dec. 1, 2011; and is being submitted via EFS-Web with the filing of the specification.

BACKGROUND OF THE INVENTION

Monitoring ligand-receptor interactions is of paramount importance for the development of sensor platforms used in threat detection. To date, these devices have been bulky, insensitive, and/or difficult to use. For example, surface plasmon resonance (SPR) spectrometry requires an expensive, dedicated instrument and a trained operator. Moreover, the instrument is not easily portable and has only modest sensitivity. SPR also requires that the experiment be performed on a substrate with a thin gold film, which is used as the sensing element. Newer plasmonic assays, which are based on nanoparticles, can circumvent some of these difficulties, but often require amplification steps and are generally less sensitive than fluorescence-based detection, which is often capable of single molecule sensitivity. Moreover, fluorescence assays can be made compatible with portable, battery-operated, hand-held devices. Unfortunately, fluorescence measurements typically require that analytes of interest be labeled in order to make a measurement. This makes fluorescence strategies challenging and often impractical for many biosensor applications.

A need exist for simple, rapid, and effective methods and systems for detecting binding interactions. The present invention fulfills this need and provides further related advantages.

SUMMARY OF THE INVENTION

The present invention provides fluorescent-based methods and systems for detecting binding between two molecules.

In one aspect, the invention provides a method for detecting binding between a first molecule and a second molecule. In one embodiment, the method includes obtaining a first fluorescence measurement of a pH-sensitive fluorophore-labeled molecule; contacting the pH-sensitive fluorophore-labeled molecule with a second molecule, wherein the second molecule is a non-fluorescently-labeled molecule; and obtaining a second fluorescence measurement of the pH-sensitive fluorophore-labeled molecule, wherein a change in fluorescence between the first and second measurements is indicative of binding of the pH-sensitive fluorophore-labeled molecule to the second molecule.

In one embodiment, the pH-sensitive fluorophore-labeled molecule and the second molecule are in solution. In another embodiment, one of the pH-sensitive fluorophore-labeled molecule or the second molecule is immobilized on a substrate.

In one embodiment, the pH-sensitive fluorophore-labeled molecule is a pH-sensitive fluorophore-labeled receptor and the second molecule is a ligand. In another embodiment, the pH-sensitive fluorophore-labeled molecule is a pH-sensitive fluorophore-labeled ligand and the second molecule is a receptor.

In one embodiment, the pH-sensitive fluorophore-labeled molecule is a pH-sensitive fluorophore-labeled PNA and the second molecule is a DNA. In another embodiment, the pH-sensitive fluorophore-labeled molecule is a pH-sensitive fluorophore-labeled DNA and the second molecule is a PNA.

In one embodiment, the pH-sensitive fluorophore-labeled molecule is an ortho-sulforhodamine 101-labeled molecule. In one embodiment, the pH-sensitive fluorophore-labeled molecule is an ortho-sulforhodamine 101-labeled molecule that is substantially free of para-sulforhodamine 101-labeled molecule.

In a further embodiment, the invention provides a method for detecting binding between a protein nucleic acid (PNA) and a deoxyribonucleic acid (DNA). In one embodiment, the method includes obtaining a first fluorescence measurement of a first solution comprising a PNA; introducing a second solution comprising a DNA to the first solution to form a third solution, wherein the PNA or the DNA, but not both, is labeled with a pH-sensitive fluorophore; and obtaining a second fluorescence measurement of the third solution, wherein a change in fluorescence between the first and second fluorescence measurements is indicative of binding of the PNA and the DNA to form a PNA/DNA complex.

In one embodiment, the PNA is labeled with a pH-sensitive fluorophore.

In one embodiment, the pH-sensitive fluorophore is ortho-sulforhodamine 101 and the PNA or the DNA labeled with the pH-sensitive fluorophore is substantially free of PNA or the DNA labeled with para-sulforhodamine 101. In one embodiment, the method further comprises employing either para-sulforhodamine 101-labeled PNA or para-sulforhodamine 101-labeled DNA as a reference.

In one embodiment, the method further includes measuring a melting curve of the PNA/DNA complex.

In one embodiment, the third solution has a pH ranging within about 1 to about 2 pH units of the pKa of the pH-sensitive fluorophore.

In one embodiment, each solution is an aqueous solution that does not include organic solvent.

In one embodiment, the method further comprises adding $Hg^{2+}$ to the third solution to obtain a fourth solution; and obtaining a third fluorescence measurement of the fourth solution, wherein a change in fluorescence between the second and third fluorescence measurements is indicative of the binding of $Hg^{2+}$ to the PNA/DNA complex. In one embodiment of this method, each solution is an aqueous solution that does not include organic solvent.

In another aspect, the invention provides a method for detecting binding between a first molecule and a second molecule in which neither molecule is labeled with fluorophore (e.g., a pH-sensitive fluorophore). In one embodiment, the method includes obtaining a first fluorescence measurement of a pH-sensitive fluorophore-labeled substrate and a first non-fluorescently-labeled molecule; contacting the pH-sensitive fluorophore-labeled substrate with a second non-fluorescently-labeled molecule in the presence of the first molecule; and obtaining a second fluorescence measurement of the pH-sensitive fluorophore-labeled substrate, wherein a change in fluorescence between the first and second measurements is indicative of binding of the first molecule to the second molecule.

In one embodiment, the first molecule is a receptor and the second molecule is a ligand. In another embodiment, the first molecule is a ligand and the second molecule is a receptor.

In one embodiment, the first molecule is a PNA and the second molecule is a DNA. In another embodiment, the first molecule is a DNA and the second molecule is a PNA.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1:
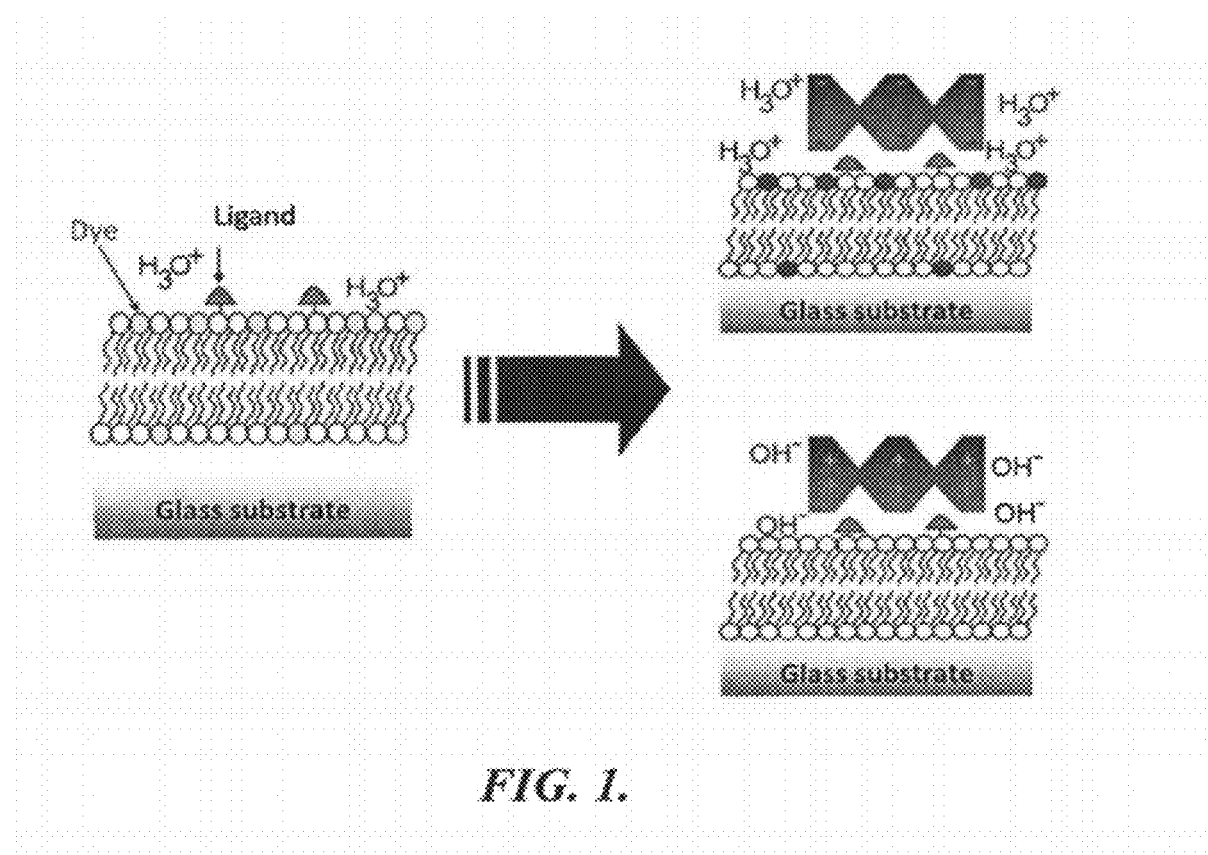
FIG. 1 is a schematic illustration of a pH modulation assay using a lipid bilayer construct. The right-hand image shows a supported lipid bilayer containing lipid-conjugated ligands (triangles) and lipid-conjugated dye molecules. Upon the binding of a negatively charged protein, the dye molecules are protonated (upper-right image). Upon binding of a positively charged protein, the dye becomes deprotonated (lower-right image). These are "turn-on" and "turn-off" assays, respectively.

The present invention provides methods and systems for detecting binding of two entities (e.g., two binding partners or members of a binding pair) by measuring local pH modulation using a pH-sensitive fluorophore.

In certain embodiments, detection methods are provided where there is not a need for labeling either binding member of a binding pair, though either may optionally be labeled. In other embodiments, one member of each binding pair is labeled with a pH-sensitive fluorophore for the purpose of detecting binding.

As used herein, "pH-sensitive fluorophore" or "pH-sensitive dye" are used interchangeably and refer to a fluorophore (or dye) having a fluorescent emission intensity that is sensitive to the pH environment of the fluorophore (or dye). Suitable pH-sensitive fluorophores have a first fluorescence emission intensity at a first pH and a second fluorescence emission intensity at a second pH, wherein the first and second pH are not the same and the first and second intensities are not the same. The emission wavelength maxima for the first and second fluorescent emissions are substantially the same (e.g., ±10 nm) Preferred pH-sensitive fluorophores have a relatively great difference in first and second emission intensities over a relatively small pH range. In one embodiment, the first fluorescence emission intensity is greater than the second fluorescence emission intensity when the first pH is greater than the second pH. In another embodiment, the first fluorescence emission intensity is greater than the second fluorescence emission intensity when the first pH is less than the second pH.

In certain embodiments, pH-sensitive dyes useful in the methods and systems of the invention include those that are substantially non-fluorescent at neutral pH and highly fluorescent, preferably at red wavelengths (e.g., greater than about 570 nm) at acidic pH. In addition to having pH-sensitive fluorescent properties, useful pH-sensitive fluorophores exhibit a high resistance to photobleaching (e.g., a photobleaching-resistant pH-sensitive fluorophore). In some embodiments, a photobleaching-resistant pH-sensitive fluorophore corresponds to a resistance that is at least two orders of magnitude more stable than coumarin 102, as set forth in Table 1, Eggeling, C., et al., *Anal. Chem.*, 70:2651-2659, 1988.

A representative pH-sensitive dye useful in the systems and methods of the invention is pHrodo™, which is commercially available from Life Technologies, Invitrogen. pHrodo™ dye is a rhodamine-based, fluorogenic dye that dramatically increases in fluorescence as the pH of its surroundings becomes more acidic. The amine-reactive succinimidyl ester form of this dye (pHrodo™ SE) has a pKa of about 7.3 in solution, which shifts to about 6.5 upon conjugation to the K-12 strain of *E. coli* or the protein A-free Wood strain of *S. aureus* used in this product line. The optimal absorption and fluorescence emission maxima of the pHrodo™ dye and its conjugates is approximately 560 nm and 585 nm, respectively. However, the dye is readily excited with the 488 nm argon-ion laser installed on most flow cytometers, microscopes and microplate readers.

Other representative pH-sensitive dyes useful in the systems and methods of the invention include rhodamine 6G, TMR, rhodamine 123, and ortho-sulforhodamine 101. In some embodiments, the pH-sensitive fluorophore comprises a rhodamine moiety. In certain embodiments, fluorescein, coumarin, and their derivatives are useful in the methods of the invention.

In some embodiments, the pH sensitivity of a pH-sensitive fluorophore is about 2, 2.5, 3, 3.5, 4, 4.5, 5, 5.5, 6, 6.5, 7, 7.5, 8, 8.5, 9, 9.5, 10, 10.5, 11, 11.5, 12, 12.5, or 13, or any range derivable therein. The pH sensitivity of a given fluorophore may be altered by, for example, adding negative or positive charge to a surface in the environment of the fluorophore (e.g., adding negatively or positively charged lipids to a lipid surface).

In the practice of the methods of the invention, a change in the fluorescence of a pH-sensitive fluorophore is observed upon binding of two binding entities (binding members or partners of a binding pair) (e.g., first and second molecule binding such as receptor-ligand binding, protein nucleic acid-nucleic acid (PNA-DNA) binding, mercury (II) (or mercuric ion, $Hg^{2+}$) binding to a PNA/DNA complex). The change may be small as less than 3 parts in 1,000 at the 99% confidence level, for example. The change may be expressed in terms of percentage, such as a change of about 0.5, 1, 1.5, 2, 2.5, 3, 3.5, 4, 4.5, 5, 5.5, 6, 6.5, 7, 7.5, 8, 8.5, 9, 9.5, or 10% or more. In certain embodiments, the change can be several fold (e.g., 2×, 3×, 4×, 5×, 6×, 7×, 8×, 9×, 10×, or more).

As used herein, the a "pH-insensitive fluorophore" refers to a fluorophore that does not exhibit a change in fluorescence over the pH range of the experimental conditions employed, or exhibits a maximum change of less than 5%. pH-Insensitive fluorophores are well-known in the art. An example of a pH-insensitive fluorophore is para-sulforhodamine 101.

In one aspect, the invention provides a method for detecting binding between a first molecule and a second molecule. In one embodiment, the method includes obtaining a first fluorescence measurement of a pH-sensitive fluorophore-labeled molecule; contacting the pH-sensitive fluorophore-labeled molecule with a second molecule, wherein the second molecule is a non-fluorescently-labeled molecule; and obtaining a second fluorescence measurement of the pH-sensitive fluorophore-labeled molecule, wherein a change in fluorescence between the first and second measurements is indicative of binding of the pH-sensitive fluorophore-labeled molecule to the second molecule.

In one embodiment, the pH-sensitive fluorophore-labeled molecule and the second molecule are in solution. In another embodiment, one of the pH-sensitive fluorophore-labeled molecule or the second molecule is immobilized on a substrate.

In one embodiment, the pH-sensitive fluorophore-labeled molecule is a pH-sensitive fluorophore-labeled receptor and the second molecule is a ligand. In another embodiment, the pH-sensitive fluorophore-labeled molecule is a pH-sensitive fluorophore-labeled ligand and the second molecule is a receptor.

In one embodiment, the pH-sensitive fluorophore-labeled molecule is a pH-sensitive fluorophore-labeled PNA and the second molecule is a DNA. In another embodiment, the pH-sensitive fluorophore-labeled molecule is a pH-sensitive fluorophore-labeled DNA and the second molecule is a PNA.

In one embodiment, the pH-sensitive fluorophore-labeled molecule is an ortho-sulforhodamine 101-labeled molecule. In one embodiment, the pH-sensitive fluorophore-labeled molecule is an ortho-sulforhodamine 101-labeled molecule that is substantially free of para-sulforhodamine 101-labeled molecule.

In a further embodiment, the invention provides a method for detecting binding between a protein nucleic acid (PNA) and a deoxyribonucleic acid (DNA). In one embodiment, the method includes obtaining a first fluorescence measurement of a first solution comprising a PNA; introducing a second solution comprising a DNA to the first solution to form a third solution, wherein the PNA or the DNA, but not both, is labeled with a pH-sensitive fluorophore; and obtaining a second fluorescence measurement of the third solution, wherein a change in fluorescence between the first and second fluorescence measurements is indicative of binding of the PNA and the DNA to form a PNA/DNA complex.

In one embodiment, the PNA is labeled with a pH-sensitive fluorophore.

In one embodiment, the pH-sensitive fluorophore is ortho-sulforhodamine 101 and the PNA or the DNA labeled with the pH-sensitive fluorophore is substantially free of PNA or the DNA labeled with para-sulforhodamine 101. In one embodiment, the method further comprises employing either para-sulforhodamine 101-labeled PNA or para-sulforhodamine 101-labeled DNA as a reference.

In one embodiment, the method further includes measuring a melting curve of the PNA/DNA complex.

In one embodiment, the third solution has a pH ranging within about 1 to about 2 pH units of the pKa of the pH-sensitive fluorophore.

In one embodiment, each solution is an aqueous solution that does not include organic solvent.

In one embodiment, the method further comprises adding $Hg^{2+}$ to the third solution to obtain a fourth solution; and obtaining a third fluorescence measurement of the fourth solution, wherein a change in fluorescence between the second and third fluorescence measurements is indicative of the binding of $Hg^{2+}$ to the PNA/DNA complex. In one embodiment of this method, each solution is an aqueous solution that does not include organic solvent.

In one embodiment, the invention provides a method of detecting binding between a first molecule and a second molecule, comprising obtaining a first fluorescence measurement of a first solution comprising a first molecule defined as a pH-sensitive fluorophore-labeled molecule; introducing a second solution comprising a second molecule to the first solution to produce a third solution, wherein the second molecule is a non-fluorescently-labeled molecule; and obtaining a second fluorescence measurement of the third solution, wherein a change in fluorescence between the first and second measurements is indicative of binding. The first and/or second fluorescent measurement can be made by a fluorimeter (e.g., a portable, hand-held, or battery-operated fluorometer).

In certain embodiments, the pH-sensitive fluorophore-labeled molecule is an ortho-sulforhodamine 101-labeled molecule and the ortho-sulforhodamine 101-labeled molecule is substantially free of para-sulforhodamine 101-labeled molecule. In one embodiment, the first solution is substantially free of para-sulforhodamine 101-labeled molecule. In certain embodiments, the method further comprises employing para-sulforhodamine 101-labeled molecule as a reference. In certain embodiments, the pH-sensitive fluorophore-labeled molecule is a pHrodo™-labeled molecule.

In some embodiments, the pH-sensitive fluorophore-labeled molecule is a pH-sensitive fluorophore-labeled receptor. In certain embodiments, the second molecule is a ligand (e.g., DNA or PNA). In some embodiments, the pH-sensitive fluorophore-labeled molecule is a pH-sensitive fluorophore-labeled PNA. In some embodiments, the pH-sensitive fluorophore-labeled molecule is a pH-sensitive fluorophore-labeled DNA.

In some embodiments, the first molecule is a pH-sensitive fluorophore-labeled PNA and the second molecule is non-fluorescently labeled DNA.

In some embodiments, the first molecule is a pH-sensitive fluorophore-labeled DNA and the second molecule is a non-fluorescently labeled PNA.

In certain embodiments, a substance is added to the third solution after obtaining the second fluorescence measurement to produce a fourth solution. In some embodiments, the method includes determining whether $Hg^{2+}$ is present in the fourth solution by obtaining a third fluorescence measurement of the fourth solution, wherein a change in fluorescence between the second and third fluorescence measurements is indicative of the presence of $Hg^{2+}$ in the fourth solution.

As noted above, the methods of the invention detect binding between molecules and rely on measuring local pH changes that occur upon binding. Some embodiments provide a method of detecting binding between a protein nucleic acid (PNA) and a deoxyribonucleic acid (DNA). In one embodiment, this method includes obtaining a first fluorescence measurement of a first solution comprising a PNA; introducing a second solution comprising a DNA to the first solution to form a third solution, wherein either the PNA or the DNA, but not both, is labeled with a pH-sensitive fluorophore; and obtaining a second fluorescence measurement of the third solution, wherein a change in fluorescence between the first and second fluorescence measurements is indicative of binding of the PNA and the DNA to form a PNA/DNA complex.

The PNA may range in size from 3 to 100 N-(2-aminoethyl)-glycine-containing units, each of which may be the same or different. It is noted that the larger the PNA, the stronger the binding affinity. In some embodiments, the affinity is sufficiently low that binding only occurs in the presence of $Hg^{2+}$. In some embodiments, the PNA is labeled with a pH-sensitive fluorophore. In some embodiments, one or more PNAs, such as each PNA, is labeled with only one pH-sensitive fluorophore. In some embodiments, one or more PNAs, such as each PNA, is labeled with only two pH-sensitive fluorophores. In some embodiments, the pH-sensitive fluorophore is ortho-sulforhodamine 101 and the first solution is substantially free of para-sulforhodamine 101-conjugate. In some embodiments, the method further comprises employing either para-sulforhodamine 101-labeled PNA or para-sulforhodamine 101-labeled DNA as a reference. In some embodiments, the pH-sensitive fluorophore is pHrodo™.

In some embodiments, a method may further comprise measuring a melting curve of the PNA/DNA complex.

In some embodiments, the third solution has a pH ranging within about 1 to about 2 pH units of the pKa value of the pH sensitive fluorophore. In some embodiments, one or more of the solutions (e.g., each solution) is an aqueous solution that does not include an organic solvent. In some embodiments, the PNA/DNA complex comprises a thymine-thymine double mismatch.

In certain embodiments, the methods of the invention include detecting the binding of $Hg^{2+}$ by the PNA/DNA complex. In one embodiment of the method, $Hg^{2+}$ is added to the third solution to obtain a fourth solution; and a third fluorescence measurement of the fourth solution is obtained. A change in fluorescence between the second and third fluorescence measurements is indicative of the binding of $Hg^{2+}$ to the PNA/DNA complex to form a PNA/DNA/$Hg^{2+}$ complex. In certain embodiments, the methods of the invention are effective to measure the dissociation ($K_d$) of the PNA/DNA/$Hg^{2+}$ complex.

In certain embodiments, the methods of the invention include detecting an interferent in the fourth solution. As used herein, "interferent" refers to a metals cation (e.g., a divalent metal cation) that interferes with $Hg^{2+}$ binding. Representative divalent metal cation interferents include $Co^{2+}$, $Mn^{2+}$, $Pb^{2+}$, and $Zn^{2+}$.

In the above methods, one or more of the solutions (e.g., each solution) is an aqueous solution that does not include an organic solvent.

In another embodiment, the invention provides a method of detecting $Hg^{2+}$ in a solution. In one embodiment, the method includes obtaining a first fluorescence measurement of a solution comprising a PNA/DNA complex, wherein either the PNA or the DNA, but not both, is labeled with a pH-sensitive fluorophore; introducing $Hg^{2+}$ to the first solution to obtain a second solution; and obtaining a second fluorescence measurement of the second solution, wherein a change in fluorescence between the first and second fluorescence measurements is indicative of the presence of $Hg^{2+}$ in the second solution.

In a related method, the invention provides a method for determining whether $Hg^{2+}$ is present in a solution. In one embodiment, the method includes obtaining a first fluorescence measurement of a first solution comprising a PNA/DNA complex, wherein either the PNA or the DNA, but not both, is labeled with a pH-sensitive fluorophore; introducing a substance to the first solution to produce a second solution, wherein the substance may or may not include $Hg^{2+}$, or may or may not yield $Hg^{2+}$ upon introduction to the first solution; and obtaining a second fluorescence measurement of the second solution, wherein a change in fluorescence between the first and second fluorescence measurements is indicative of the presence of $Hg^{2+}$ in the second solution. In embodiments of the method for detecting $Hg^{2+}$, a PNA/DNA complex is typically formed first, followed by the addition of $Hg^{2+}$.

In embodiments of the methods described above, one or more (e.g., each) solution is an aqueous solution that does not include an organic solvent and one or more (e.g., each) solution or binding partner (e.g., ligand, receptor, or substrate) may not include any or any additional pH-sensitive fluorophore or other fluorophore.

In embodiments of the methods described above, one member of the binding pair may be labeled with a pH-sensitive fluorophore and the other is not labeled with a pH-sensitive fluorophore or any other fluorophore. In embodiments of the methods described above, both members of a binding pair may be unlabeled with a pH-sensitive fluorophore or any other fluorophore. In homogeneous conditions, one member of the binding pair is labeled with a pH-sensitive fluorophore.

In embodiments of the methods described above, one or more (e.g., each) solution is substantially free of ortho-sulforhodamine 101 and one or more (e.g., each) solution is substantially free of para-sulforhodamine 101.

In other embodiments, the invention provides a method for detecting binding between a non-fluorescently labeled receptor and a non-fluorescently labeled ligand. The method includes obtaining a first fluorescence measurement associated with a substrate comprising both a pH-sensitive fluorophore (e.g., pHrodo™) and the non-fluorescently labeled receptor; introducing a solution comprising the non-fluorescently labeled ligand to the substrate; and obtaining a second fluorescence measurement, wherein a change in fluorescence between the first and second measurements is indicative of binding.

In other embodiments, the invention provides a method for detecting binding between a non-fluorescently labeled ligand and a non-fluorescently labeled receptor. The method includes obtaining a first fluorescence measurement associated with a substrate comprising both a pH-sensitive fluorophore (e.g., pHrodo™) and the non-fluorescently labeled ligand; introducing a solution comprising the non-fluorescently labeled receptor to the substrate; and obtaining a second fluorescence measurement, wherein a change in fluorescence between the first and second measurements is indicative of binding.

In other embodiments, the invention provides a method for detecting binding between a ligand and a receptor. The method includes obtaining a first fluorescence measurement of a first solution comprising a pH-sensitive fluorophore labeled receptor (e.g., pHrodo™-labeled receptor); introducing a second solution comprising a ligand; and obtaining a second fluorescence measurement, wherein a change in fluorescence between the first and second measurements is indicative of binding.

In other embodiments, the invention provides a method for determining a kinetic measurement of a receptor-ligand binding event. The method includes contacting a pH-sensitive fluorophore labeled protein (e.g., pHrodo™-labeled protein) with a ligand, wherein $k_{on}$ for the binding event is determined.

In other embodiments, the invention provides a method for detecting binding between a non-fluorescently labeled PNA and a non-fluorescently labeled DNA. The method includes obtaining a first fluorescence measurement associated with a substrate comprising both a pH-sensitive fluorophore and the non-fluorescently labeled PNA; introducing a first solution comprising the non-fluorescently labeled DNA to the substrate to form a PNA/DNA complex in a second solution; and obtaining a second fluorescence measurement of the second solution, wherein a change in fluorescence between the first and second measurements is indicative of binding. In some embodiments, a method further comprises detecting the binding of $Hg^{2+}$ by the PNA/DNA complex in a method that includes adding $Hg^{2+}$ to the second solution to obtain a third solution; and obtaining a third fluorescence measurement of the third solution, wherein a change in fluorescence between the second and third fluorescence measurements is indicative of the binding of $Hg^{2+}$ to the PNA/DNA complex to form a PNA/DNA/$Hg^{2+}$ complex.

In other embodiments, the invention provides a method for detecting binding between a non-fluorescently labeled PNA and a pH-sensitive fluorophore-labeled DNA. The method includes obtaining a first fluorescence measurement of a first solution comprising a non-fluorescently labeled PNA; introducing a second solution comprising a pH-sensitive fluorophore-labeled DNA to the first solution to form a third solution; and obtaining a second fluorescence measurement of the third solution, wherein a change in fluorescence between the first and second fluorescence measurements is indicative of binding of the non-fluorescently labeled PNA and the pH-sensitive fluorophore-labeled DNA to form a PNA/DNA complex.

In other embodiments, the invention provides a method for detecting $Hg^{2+}$ in a solution. The method includes obtaining a first fluorescence measurement of a solution comprising a non-fluorescently labeled PNA/pH-sensitive fluorophore-labeled DNA complex; introducing $Hg^{2+}$ to the first solution to obtain a second solution; and obtaining a second fluorescence measurement of the second solution, wherein a change in fluorescence between the first and second fluorescence measurements is indicative of the presence of $Hg^{2+}$ in the second solution.

In other embodiments, the invention provides a method for determining whether $Hg^{2+}$ is present in a solution. The method includes obtaining a first fluorescence measurement of a first solution comprising a non-fluorescently labeled PNA/pH-sensitive fluorophore-labeled DNA complex; introducing a substance to the first solution to produce a second solution, wherein the substance may or may not comprise $Hg^{2+}$ or may or may not yield $Hg^{2+}$ upon introduction to the first solution; and obtaining a second fluorescence measurement of the second solution, wherein a change in fluorescence between the first and second fluorescence measurements is indicative of the presence of $Hg^{2+}$ in the second solution.

Any method described herein may be used as a high throughput screening method.

The methods of the invention can be modified to include the addition of positively or negatively charged lipids to a supported lipid bilayer such that the pH-sensitive fluorophore employed in the method reacts differently to a receptor-ligand binding event.

In another aspect, the invention provides a method for detecting binding between a first molecule and a second molecule in which neither molecule is labeled with fluorophore (e.g., a pH-sensitive fluorophore). In one embodiment, the method includes obtaining a first fluorescence measurement of a pH-sensitive fluorophore-labeled substrate and a first non-fluorescently-labeled molecule; contacting the pH-sensitive fluorophore-labeled substrate with a second non-fluorescently-labeled molecule in the presence of the first molecule; and obtaining a second fluorescence measurement of the pH-sensitive fluorophore-labeled substrate, wherein a change in fluorescence between the first and second measurements is indicative of binding of the first molecule to the second molecule.

In one embodiment, the first molecule is a receptor and the second molecule is a ligand. In another embodiment, the first molecule is a ligand and the second molecule is a receptor.

In one embodiment, the first molecule is a PNA and the second molecule is a DNA. In another embodiment, the first molecule is a DNA and the second molecule is a PNA.

In other aspects, the invention provides a substrate labeled with pH-sensitive fluorophores.

In one embodiment, the substrate includes (a) a pH-sensitive fluorophore conjugate (e.g., pHrodo™-conjugate); and (b) a ligand or a receptor. In another embodiment, the substrate includes (a) a pH-sensitive fluorophore-containing moiety; and (b) a PNA or a DNA.

In one embodiment, the substrate is a bead having a coating, wherein the coating comprises a surface that includes a pH-sensitive fluorophore or conjugate (e.g., pHrodo™-or conjugate). In another embodiment, the bead has a coating that includes a surface that having a pH-sensitive fluorophore or conjugate (e.g., pHrodo™ or conjugate) covalently bound to both the coating and to a first ligand or a first receptor, or covalently bound to both the coating and to a PNA or a DNA.

In certain embodiments, the substrate is planar. The substrate may comprise plastic, glass (e.g., borosilicate), silica, mica, sapphire, a polymer, or an oxide, or a combination thereof. Non-limiting examples of oxides include alumina and $TiO_2$, and others are known in the art. The substrate may comprise a polymer, such as polydimethylsiloxane (PDMS). In some embodiments, PDMS is exposed to an oxygen plasma such that the surface is hydrophilic. In some embodiments, the PDMS is used within about fifteen minutes of being exposed to an oxygen plasma for this purpose. In some embodiments, the substrate comprises a semiconductor. The substrate may comprise a lipid. In some embodiments, the substrate comprises a supported lipid bilayer. In other embodiments, the substrate does not include a supported lipid bilayer. In some embodiments, the substrate is free of any other fluorophore or fluorophore-containing conjugate. The substrate may be a well of a multi-well plate (e.g., 96-well or 384-well). The substrate may be comprised in a device, such as a microfluidic device. For example, the substrate may be the surface of a microfluidic device (e.g., channel).

In other embodiments, the substrate is a bead. The skilled artisan will realize that the invention is not limited to spherical beads and any shaped bead or particle may be used. The terms "bead" and "particle" are used interchangeably herein to signify that any shaped bead or particle may be used in the invention. Beads may be spherical but may also be other shapes, such as ovals, cubes, closed cylinders and irregular shapes. Beads may be porous or non-porous. A bead may be a silica bead or a polystyrene bead. The diameter of a bead may range from about 0.05 μm to about 100 μm. In some embodiments, the diameter ranges from about, at most about, or at least about 0.05, 0.1, 0.5, 1.0, 10, 50, or 100 μm, or any range derivable therein. A bead may be substantially covered by a coating. The coating may be a protein-resistant coating, which, as is known in the art, is a material that resists the binding of a protein. The protein-resistant coating may comprise zwitterionic lipids, polyethyleneglycol (PEG), or a mixture thereof. Molecular weights of PEG may range from small oligomers (e.g., a 5-mer) to values (e.g., $PEG^{10,000}$). A pH-sensitive fluorophore or conjugate (e.g., pHrodo™ or conjugate) may be immobilized on the coating. A conjugate may be immobilized such that the fluorophore is presented on the surface of the coating. In some embodiments, the pH-sensitive fluorophore conjugate is covalently bound to the coating such that the pH-sensitive fluorophore is presented on the surface of the coating.

In some embodiments, the pH-sensitive fluorophore conjugate (e.g., pHrodo™-conjugate) includes the ligand or receptor to form a labeled ligand or a labeled receptor. In some embodiments, the conjugate comprises the receptor to form a labeled receptor. The conjugate may be covalently bound to the substrate such that the conjugate is presented on the surface of the coating. The pH-sensitive fluorophore may be covalently bound to the substrate and to either the ligand or the receptor.

In some embodiments, the pH-sensitive fluorophore-conjugate comprises a lipid, such as DHPE. In some embodiments, the conjugate comprises a polymer, such as PEG.

In some embodiments, the pH-sensitive fluorophore is not encapsulated. For example, in some embodiments, the conjugated or unconjugated fluorophore is not encapsulated in a solution in a liposome, bead, or other encapsulating body. In some embodiments, the conjugated or unconjugated fluorophore is not encapsulated by means of being presented on the interior surface of a liposome, bead, or other encapsulating body. In some embodiments, the detection of a change of fluorescence takes place external to a liposome, bead, or other encapsulating body. In some embodiments, the ligand does not comprise a fluorophore. In some embodiments, the receptor does not comprise a fluorophore. In some embodiments, the ligand is not a metal ion. In some embodiments, a receptor is a non-fluorescently labeled receptor. In some embodiments, a ligand is a non-fluorescently labeled ligand. In some embodiments, a PNA is defined as a non-fluorescently labeled PNA. In some embodiments, a DNA is defined as a non-fluorescently labeled DNA.

In some embodiments, a change in fluorescence upon receptor-ligand binding is not dependent upon the release of a species from a substrate. In some embodiments, a fluorophore presented on the surface of a bead or other substrate is not coated with a second lipid layer, such as described by U.S. Pat. No. 7,514,267, incorporated herein by reference. In some embodiments, a coating on a substrate is not a metal coating.

In some embodiments, the present invention contemplates a bead having a coating, wherein the coating comprises a surface that comprises pH-sensitive fluorophore-conjugate, such as the conjugate presented on the surface. The conjugate may be immobilized on the coating such that the fluorophore is presented on the surface of the coating. The conjugate may be covalently bound to the coating such that the fluorophore is presented on the surface of the coating. The coating may be a protein-resistant coating, as described above. Indeed, the coating may be any coating described herein. The coating may comprise PEG. The coating may further comprise either a first ligand or a first receptor presented on the surface. The first ligand or the first receptor may be covalently bound to the coating such that it is presented on the surface of the coating. The conjugate may be covalently bound to the coating and covalently bound to a first ligand or a first receptor, such that the fluorophore and either the ligand or receptor are each presented on the surface of the coating.

In another aspect, the invention provides a system for detecting binding between a first and second molecule (e.g., receptor-ligand binding). In one embodiment, the system includes a multi-well plate and a bead labeled with a pH-sensitive fluorophore or conjugate.

In one embodiment, the invention provides a system for detecting receptor-ligand binding, comprising a multi-well plate; and a bead as described herein. The system may detect, for example, PNA binding to DNA or $Hg^{2+}$ binding to a PNA/DNA complex. The multi-well plate may be a 96- or a 384-well plate. The system may be configured to detect binding of a minimum of about 50 molecules per pixel. The system may be configured to detect binding of a minimum of about 1 part in 3,000,000 of the $K_d$ of the binding entities. In any embodiment herein, binding detection between two binding entities may be about, at least about, or at most about 1 part in 30,000,000, 1 part in 3,000,000, 1 part in 300,000, 1 part in 30,000, or 1 part in 3,000, or any range derivable therein, of the $K_d$ of binding between the two entities. The system may be configured to operate within a pH range of about 2 to about 13. In some embodiments, detection may occur at a pH of about, at most about, 2, 2.5, 3, 3.5, 4, 4.5, 5, 5.5, 6, 6.5, 7, 7.5, 8, 8.5, 9, 9.5, 10, 10.5, 11, 11.5, 12, 12.5, or 13, or any range derivable therein. As is known in the art, different pH-sensitive dyes will operate in different pH conditions. The system may operate within about one to about two pH units of the pKa value of the pH-sensitive fluorophore.

In a further aspect, the invention provides a fluidic device (e.g., a microfluidic device) that includes at least one channel labeled with a pH-sensitive fluorophore or conjugate (e.g., pHrodo™ or conjugate). The conjugate may be immobilized to the surface of the channel, as appropriate. In some embodiments, the conjugate is covalently bound to the surface of one channel. Any bead described herein may be immobilized on a surface of a channel.

Method and systems for detecting receptor-ligand binding using a pHrodo™-conjugate are also provided. In one embodiment, the method includes contacting a receptor with a ligand in the presence of a pHrodo™-conjugate, wherein a change in fluorescence of the pHrodo™-conjugate indicates binding. In certain embodiments, a pHrodo™-conjugate includes a ligand or receptor to form a pHrodo™-labeled ligand or a pHrodo™-labeled receptor. In some embodiments, the receptor is immobilized on a substrate, such as covalently bound to a substrate, and the ligand is present in a bulk aqueous phase that is introduced to the bound receptor. In some embodiments, PNA is immobilized on a substrate, such as covalently bound to a substrate, and DNA is present in a bulk aqueous phase that is introduced to the bound PNA. In some embodiments, DNA is immobilized on a substrate, such as covalently bound to a substrate, and PNA is present in a bulk aqueous phase that is introduced to the bound PNA. In some embodiments, a method further comprises a step of immobilizing the receptor to the substrate, such as covalently binding the receptor to the substrate. In some embodiments, a method further comprises a step of immobilizing the PNA or DNA to the substrate, such as covalently binding the PNA or the DNA to the substrate. In some embodiments, a method may further comprise improving receptor-ligand detection by increasing the mole percentage of the pHrodo™-conjugate immobilized to a substrate.

Kinetic measurements of receptor-ligand binding may be performed using pHrodo™-conjugates as described herein. Persons of skill in the art are familiar with kinetic experiments that may be performed using fluorophores, and such experiments may be performed using a pHrodo™-conjugate. Exemplary kinetic measurements that may be determined include the $k_{on}$ for the binding event. Stopped-flow experiments or temperature jump experiments may be employed, for example. A kinetic experiment may be performed, for example, by labeling a receptor (e.g., a protein) with pHrodo™. In some embodiments, the labeled protein is initially free in solution and the ligand, such as a small organic molecule, is also free in solution. The ligand and receptor may be mixed from separate volumes into a third chamber or, alternatively, temperature jump experiments may be performed. The ligand may be negatively charged, positively charged, or contain no net charge. In the case of negatively charged ligands, the system will typically work as a "turn-on sensor". Signal would rise in this case of binding and drop upon unbinding. The opposite would typically occur for positively charged ligands. In some embodiments, a pHrodo™-labeled protein is immobilized on a substrate. In this case, ligands can be followed over the surface to monitor binding kinetics.

In some embodiments, the invention provides a sensor that may be operated under a variety of conditions. A sensor may be configured to "turn on" when negatively charged proteins adsorb at the membrane interface near, e.g., pH 7.8. The bilayer chemistry may be tuned, according to some embodiments, to optimize the platform for a range extending from pH 4.3 to 11.3, or any other pH range described herein. Positively and negatively charged lipids, for example, may be used for this purpose. A fluorophore may turn on as the pH is increased and may be tested for use with positively charged protein analytes. It may be desirable to assess the range over which a sensor provides a linear fluorescence intensity change with changing local pH values.

In some embodiments, a pH-sensitive assay may be configured for use with one or more fluorescent bead platforms. Micron scale beads, which are typically sensitive to specific protein binding, may be made by employing silane chemistry to attach pH sensitive dye molecules and ligands. Beads may be used in a standard 96-well assay and read out with a standard fluorescence plate reader. Embodiments of this assay may be optimized for the lowest possible limits of detection and maximum resistance to non-specific protein adsorption.

Label-free biosensors may be made using supported lipid bilayer and bead-based platforms. These platforms may be fabricated using high throughput/low sample volume microfluidic techniques. Such on-chip technologies may permit the limits of detection of the pH sensor assay under a particular set of conditions to be tested (e.g., rapidly tested). New assay platforms may be fabricated within 24 hours. For example, the performance conditions may be assessed (e.g., rapidly assessed) for the optimum conditions for the best limits of detection, minimum non-specific adsorption, as well as flexibility of pH range, dye chemistry, and lipid content.

According to some embodiments of the disclosure, a simple label-free assay may be run in imaging mode for multiplexed data collection while still retaining very high sensitivity. A method may be simple to use and compatible with standard laboratory equipment such as a fluorescence microscope or plate reader. Thus, practitioners may not need to purchase a dedicated instrument or specialized assay platforms (e.g., metal coated chips). In some embodiments, an assay may be as highly sensitive as known fluorescence techniques, but without labeling the target analyte (e.g., receptor or ligand) with a fluorophore. Instead, fluorescent dyes may be directly immobilized onto the substrate surface. In some embodiments, these dyes may function as sensor elements upon specific protein binding. This may be achieved if the substrate-bound dye's fluorescence is altered (e.g., strongly enhanced) by a specific binding event.

In a further aspect, the invention provides a composition for detecting protein-ligand binding. In one embodiment, the composition includes at least one bead having a surface; at least one pH-sensitive dye-terminated PEGylated silane (e.g., pHrodo™-PEG-triethoxysilane) on the bead surface; at least one ligand-terminated PEGylated silane on the bead surface; and at least one PEGylated silane on the bead surface, wherein the at least one pH-sensitive dye-terminated PEGylated silane, the at least one ligand-terminated PEGylated silane, and the at least one PEGylated silane together substantially cover the bead surface. In another embodiment, the invention provides a composition for detecting protein-ligand binding comprising at least one bead having a surface; at least one pH-insensitive dye-terminated PEGylated silane (e.g., pHrodo™-PEG-triethoxysilane) on the bead surface; at least one ligand-terminated PEGylated silane on the bead surface; and at least one PEGylated silane on the bead surface, wherein the at least one pH-insensitive dye-terminated PEGylated silane, the at least one ligand-terminated PEGylated silane, and the at least one PEGylated silane together substantially cover the bead surface. The bead may be a glass bead, a polymer bead, an oxide substrate, a semiconductor substrate, a plastic substrate, or a supported bilayer. The diameter of the bead may be from about 0.1 μm to about 100 μm. In some embodiments, the pH sensitivity of the at least one pH-sensitive dye-terminated PEGylated silane on the bead surface is from about 2 to about 13. In some embodiments, the pH-sensitivity is of any value or range described herein.

In some embodiments, the methods of the invention detect binding of about 250 molecules per pixel. In other embodiments, the method detect binding of about 1 part in 30,000 of the $K_d$ of the binding entities.

It will be appreciated that the ability of a pH-sensitive fluorophore to detect receptor-ligand binding depends on several factors, including the photobleaching resistance of the fluorophore, the salt concentration of the bulk solution (which affects the local electric field surrounding receptor, ligand, fluorophore, and optional substrate), the concentration of receptor or ligand present (such as the concentration of receptor bound to a surface (i.e., the receptor density at a surface)), and the concentration of the fluorophore (e.g., the fluorophore density at a surface). For example, higher concentrations of the pH-sensitive fluorophore result in improved detection limits, as described herein. The level of detection will also depend on whether a reference fluorophore is employed, where employment of such a reference is expected to yield improved detection limits. Examples of such improvement are described in WO/US2010/080640. Moreover, a pH-sensitive fluorophore will respond to changes in the local electric field out to about the Debye length, which is salt concentration dependent. Under physiological conditions, this is typically 0.5 to 2 nm. However, under low salt concentrations this distance can be tens or hundreds of nanometers. Indeed, in binding detection conditions where aggregation is problematic such that a salt concentration greater than zero is needed, the Debye length will decrease. If the analyte does not aggregate such that no salt is needed, the Debye length may increase to hundreds of nanometers such that the concentration of fluorophore may be decreased and sufficient levels of detection may be still be obtained.

The following is a description of representative methods and systems of the invention.

The present invention provides a simple means of labeling substrates rather than analytes for fluorescence-based detection at the liquid/solid interface. The central idea behind the method is that the surface potential is modulated by the capture of charged analytes. This in turn modulates the $pK_A$ of nearby titratable protons on fluorescent dye molecules such as ortho-TEXAS RED®. When the analyte proteins are negatively charged, they make the surface potential more negative. This, in turn, protonates the dye molecules and "turns on" the fluorescent dye, making the assay a "turn-on" sensor. By contrast, when analyte proteins are positively charged, they make the potential more positive and hence the assay works as a "turn-off" sensor. The present invention exploits the ortho isomer of TEXAS RED® (a rhodamine derived dye) and related fluorophores for creating highly sensitive and selective assays on fluid lipid bilayers. These assays are capable of multivalent detection.

The pH modulation assays of the invention are effective for detecting proteins and may be carried out in heterogeneous assay (one working at a liquid/solid interface) and homogeneous assay (one working in a single phase bulk solution) embodiments. In practice, a local site assay would function by directly labeling protein receptor molecules with pH sensitive fluorophores. Essentially any protein with a binding pocket would therefore become a candidate for use in a pH modulation assay. The assay works to detect ions, small molecules, or protein-protein interactions. Rather than using antibodies, aptamers, or synthetically designed receptor sites, the binding pockets of proteins themselves are the recognition elements. This provides an enormous pool of untapped receptors from a vast array of species. The only requirement is that a pH-sensitive fluorescent probe can be placed in sufficiently close proximity to the binding pocket. This requirement is easily met for a large number of systems because proteins often contain free lysine residues that can be conjugated with succinimidyl ester-linked dye molecules. Indeed, many proteins contain multiple surface lysines. As long as these sites are located within the Debye length of the receptor site, then the conjugated fluorophore will be sensitive to the binding of a ligand molecule. Under physiological conditions (about 100 mM salt), the Debye length is typically on the order of 1-2 nm. Therefore, a few square nanometers of protein surface area may be probed by each dye. By analogy with surface potential measurements, negatively charged analyte ligands should work as "turn-on" sensors, while positively charged ligands should work as "turn-off" sensors. Uncharged analytes can also be detected so long as they cause sufficient allosteric effects to alter the local fields around the pH sensitive dye molecule.

Figure 2:
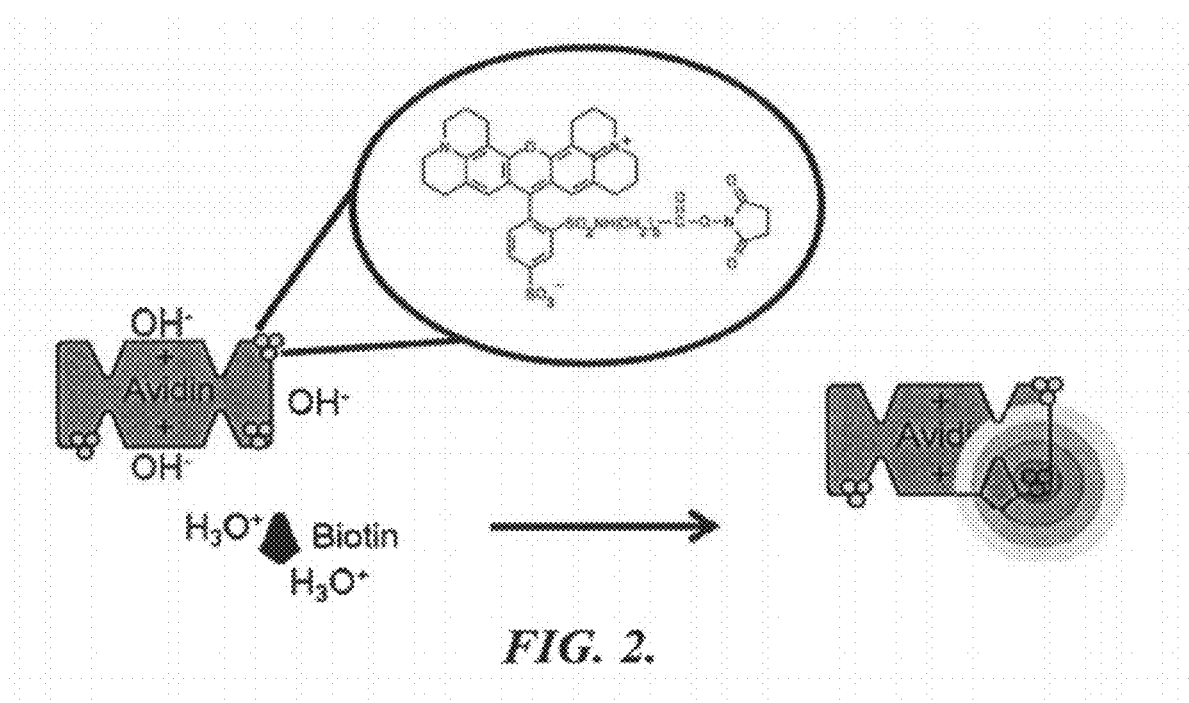
FIG. 2 is a schematic illustration of a representative protein, avidin, derivatized with ortho-TEXAS RED® at surface lysine residues. Avidin has four binding pockets for biotin (ligand). As these representative small molecules (biotin) bind, they cause the dye to become protonated and work in "turn-on" mode

A schematic diagram of the pH modulation assay applied as a local binding site probe is shown in FIG. 2. The example depicts the well-known biotin-avidin model system, which is a tight binding event. The net charge on avidin is positive and the biotin bears a charge of −1. Therefore, the sensor works in "turn-on" mode near physiological pH. There are nine lysine residues on the surface of avidin. Therefore, the binding of each biotin can activate multiple dyes.

The present invention provides local site binding assays for ligand-receptor interactions using standard protein receptor sites. The following data demonstrates the ability to monitor representative examples of ligand-receptor binding with protein kinase A, avidin, and calmodulin. These representative proteins have receptor sites for adenosine triphosphate (ATP), biotin, and calcium ions, respectively.

Protein Kinase Assays

Figure 3:
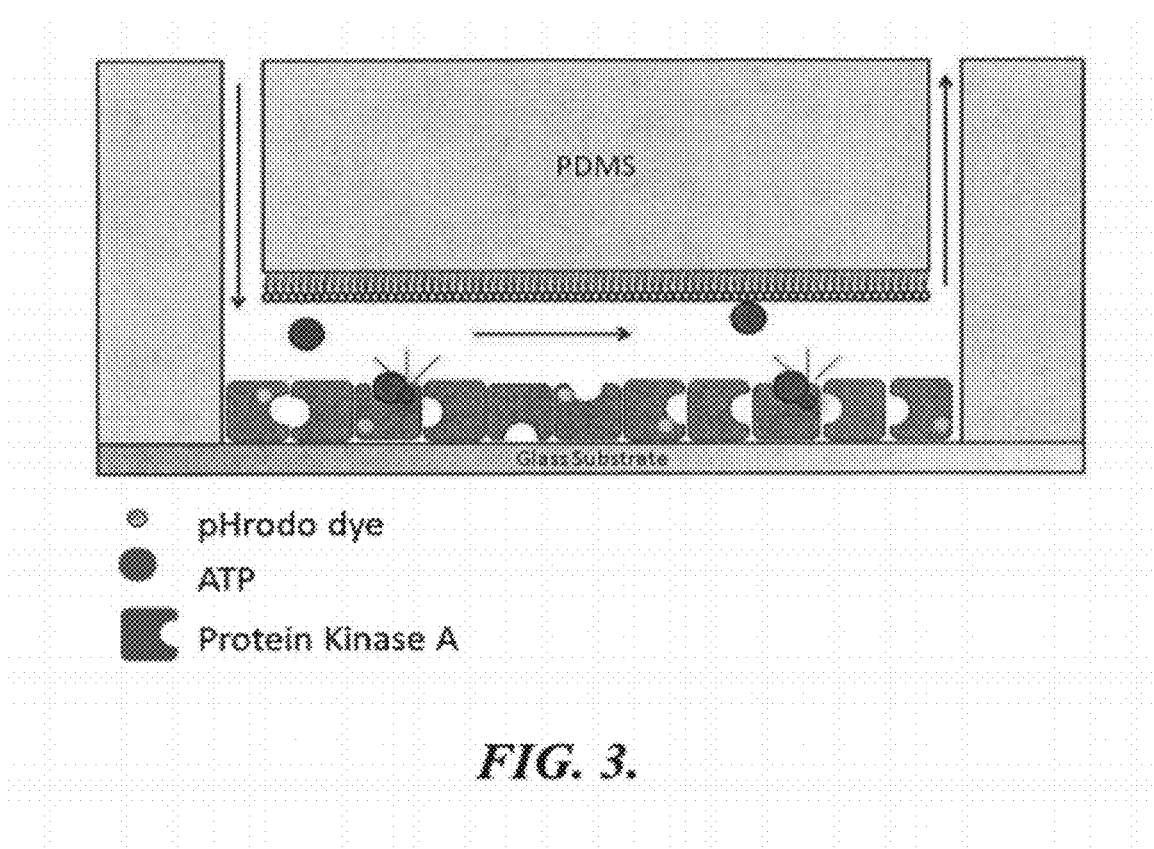
FIG. 3 is a schematic illustration a representative heterogeneous binding assay of the invention for ATP sensing. Immobilized protein kinase A on the surface of the glass substrate is conjugated with a pH-sensitive dye (e.g., pHrodo™). The analyte, ATP, is flowed over the surface.

The interaction between protein kinase A and ATP is an example of a representative local site assay. Protein kinase A is a cyclic-AMP-activated enzyme that is involved in key cellular regulation functions such as lipid metabolism. The pI of this protein is about 9.2 and the protein has a molecular weight of 40 kDa. Like other kinases, protein kinase A has an ATP binding site. This generic ATP binding motif was used to detect the presence of ATP in solution. Therefore, in a first set of assays, the kinase was immobilized on a glass substrate inside a microfluidic device (see FIG. 3). The kinase was first allowed to adsorb to the surface of a glass substrate, while the surrounding polydimethylsiloxane (PDMS) microfluidic channel was coated with a lipid bilayer to passivate the surface. Next, the succinimidyl ester of a representative pH-sensitive dye (PHRODO®) was flowed over the surface for attachment to free lysine residues. This is a red fluorescent dye much like ortho-TEXAS RED®, although its apparent $pK_A$ value is typically shifted to somewhat more acidic pH values than TEXAS RED® under similar conditions.

Figure 4:
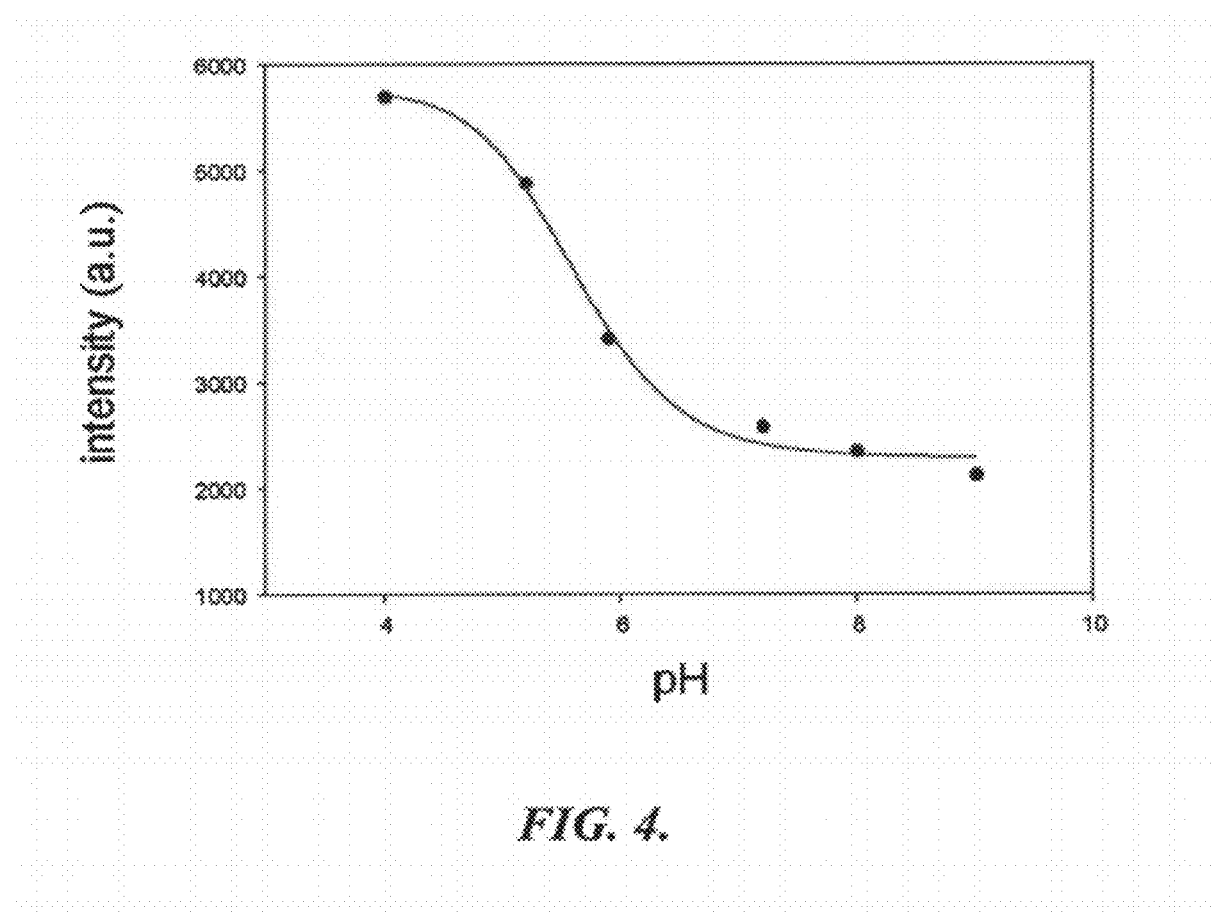
FIG. 4 is a titration curve for pHrodo™-conjugated protein kinase A having an apparent $pK_A$ for this system of about pH 5.8

The kinase includes 34 lysine residues and many of them are available for conjugation. The succinimidyl ester-conjugated pHrodo™ dye was allowed to incubate over the substrate surface at pH 8 in 30 mM $K_2HPO_4$ buffer with 150 mM KCl (KBS buffer) for 60 minutes before fresh KBS buffer was used to flow any unconjugated dye molecules out of the channels. In the next step, buffer solutions with varying pH values were flowed through the PDMS/glass microfluidic device to determine the apparent $pK_A$ of the protein-conjugated dye molecules. The results are shown in FIG. 4.

Figure 5A:
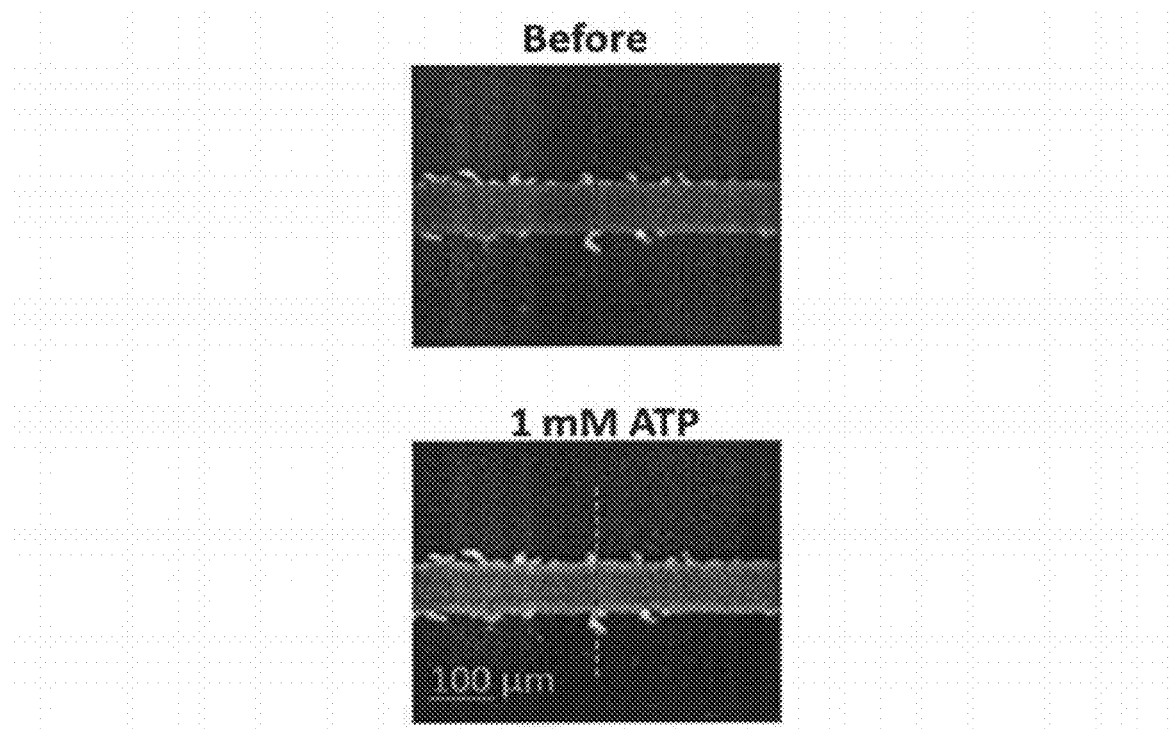
FIG. 5A are fluorescence images of a PDMS/glass microfluidic channel containing immobilized protein kinase A before (top) and after (bottom) the introduction of 1 mM ATP.
Figure 5B:
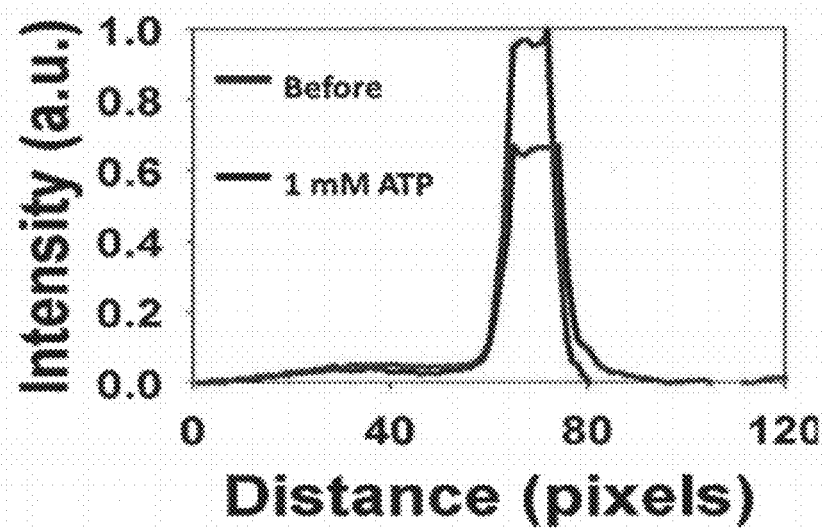
FIG. 5B compares fluorescence emission intensity in the channels illustrated in FIG. 5A.

Because the kinase bears a positive charge below pH 9.2 and the ATP molecule has 4 negative charges, the assay will work in "turn-on" mode at neutral and acidic pH values. It should be noted that different kinases have varying affinities for ATP. These values appear to be in a range from tens of nanomolar to hundreds of micromolar. As such, a concentration of 1 mM ATP at pH 7.0 was introduced in a first test of this system in order to ensure saturation binding (see FIGS. 5A and 5B). As can be seen, the fluorescence is enhanced by about 30% upon the introduction of ATP. The fluorescence intensity returns to its original level once pure buffer is again flowed through the system. A greater response would be expected when the assay is run near pH 6.3 because that is where the steepest change in fluorescence occurs as the local pH is made more acidic (see FIG. 4).

A reason for this improved sensitivity probably stems from the fact that the pH-sensitive fluorophore is on average closer to the binding analyte. In bilayer binding assays, there are fluorophores in both the upper and lower leaflets of the bilayer. Because proteins only bind to the upper leaflet in such an assay, the fluorophores in the lower leaflet will be at least 4.5 nm away from the binding event and, thus, yield a weaker response. In one embodiment, the assay can further include anti-protein kinase A antibodies pre-adsorbed onto the surface of the glass substrate and used to specifically attach the kinase molecules. In that case, the antibodies would serve a dual purpose. They would work as specific capture agents, but would also act as a sacrificial layer that would help prevent kinase denaturation. This should markedly improve the sensitivity of this heterogeneous assay.

Avidin-Biotin Binding Assays

In addition to the detection of ATP, the methods of the invention provide for the detection of a representative ligand, biotin, by using the biotin-avidin binding system. There are three key differences between this assay and the one described above for ATP. First, the biotin-avidin assay was conducted homogeneously in aqueous solution. Second, the assay was performed with ortho-TEXAS RED® rather than PHRODO® dye molecules. To do this, the succinimidyl ester of ortho-TEXAS RED® was attached to avidin via free amines on the protein's surface (see FIG. 2). The third difference between biotin and ATP detection is the significantly lower charge on the biotin of −1, which presumably makes this assay more challenging to perform.

Figure 6A:
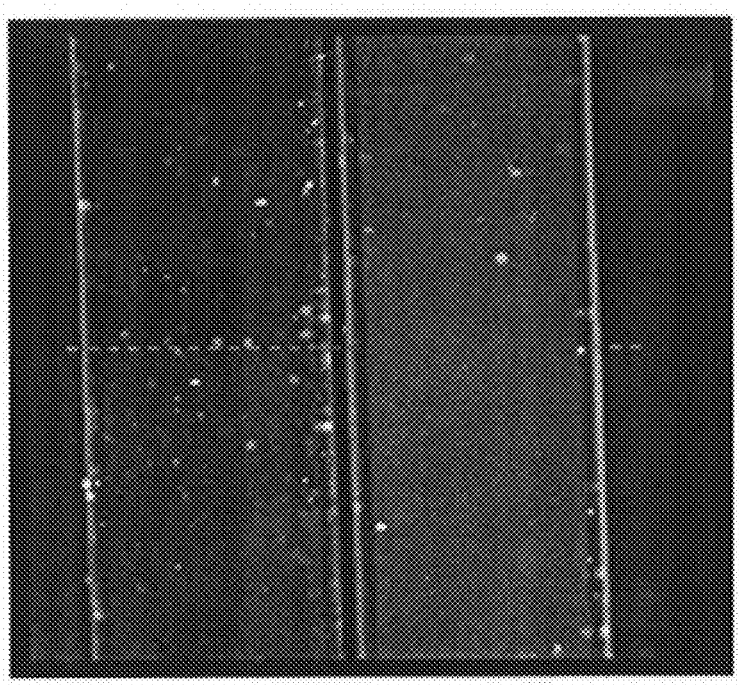
FIG. 6A is a fluorescent image of a two channel microfluidic device containing ortho-TEXAS RED® conjugated avidin. Biotin has been added to the right-hand channel, but not the left. The distance across each channel is 1 mm in length.
Figure 6B:
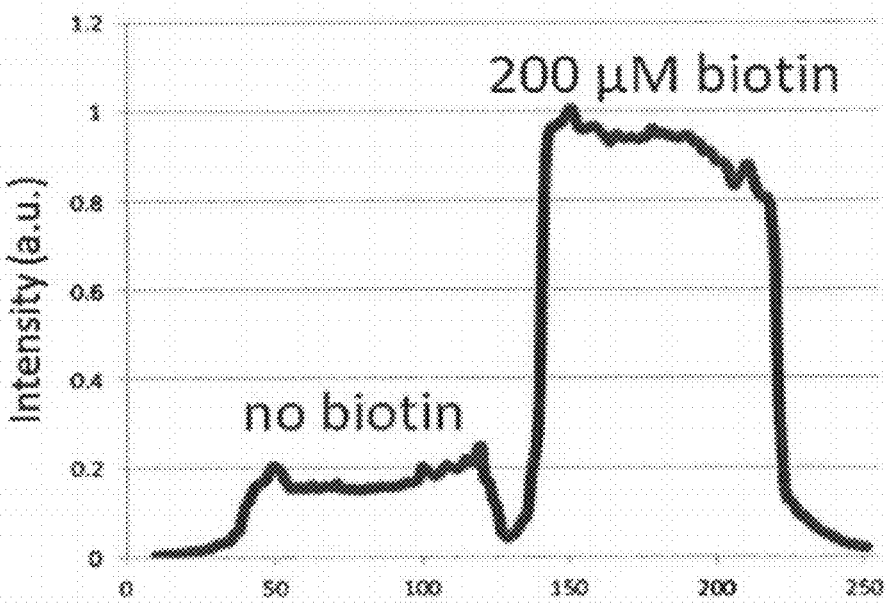
FIG. 6B compares fluorescence emission intensity in the channels (line profile across the system) illustrated in FIG. 6A.

There are nine lysine residues on the surface of avidin as well as four biotin binding pockets. Hence, the ratio of fluorophores to binding site is 2:1. Like protein kinase A, avidin bears a positive charge near physiological pH with a pI of 10.2. As such, this will also be a "turn on" sensor when run near physiological pH with a negatively charged ligand. The first assay for the detection of biotin was run in aqueous solution at pH 8.2. The fluorescence image of the two parallel microfluidic channels used for this purpose is shown in FIGS. 6A and 6B. To do this, the channels were each injected with a 10 µM solution of ortho-TEXAS RED®-conjugated avidin in phosphate buffered saline, PBS (150 mM NaCl and 10 mM phosphate buffer). Additionally, 200 µM biotin was present in the right channel, while no biotin was used on the left. A line profile across these channels is shown in FIG. 6B. As can be clearly seen, the fluorescence intensity increased by approximately a factor of six when biotin was present. The binding constant for the biotin-avidin complex is approximately 1 pM. Therefore, the conditions in FIGS. 6A and 6B represent saturation conditions.

Figure 7A:
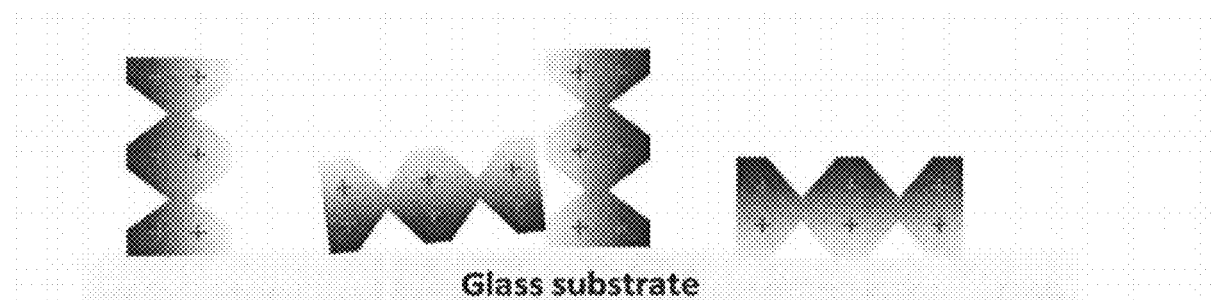
FIG. 7A is a schematic illustration of simple adsorption of a representative protein, avidin, to a planar glass substrate in which the avidin is randomly oriented on the substrate.
Figure 7B:
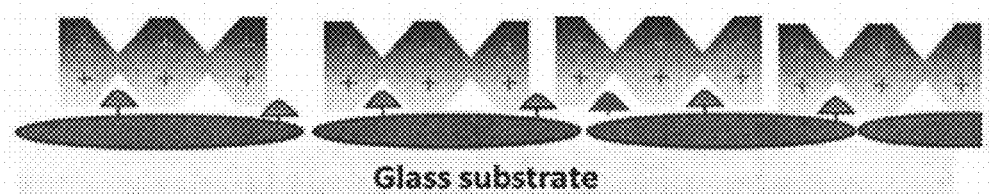
FIG. 7B is a schematic illustration of specific adsorption of avidin onto a biotinylated BSA-coated substrate in which the avidin is well oriented on the surface.
Figure 7B:
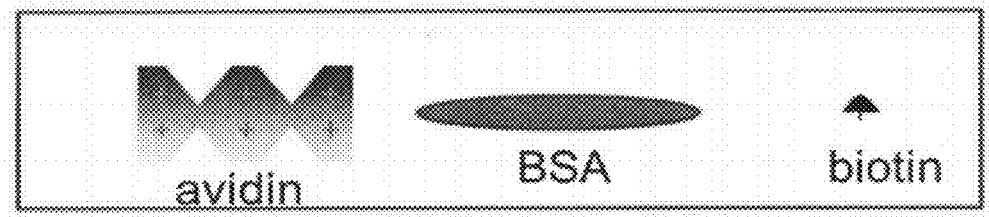

The avidin-biotin binding interaction is of particular importance as a model system because this assay can be run heterogeneously as well as homogeneously under controlled conditions. The reason that this system is advantageous for the creation of a model heterogeneous assay stems from the fact that avidin can be bound to a substrate either randomly or such that two biotin binding pockets face toward the surface while the other two face upward toward the aqueous solution. For random orientation, the protein can simply be allowed to adsorb to a glass substrate from an aqueous solution (see FIG. 7A). This will almost certainly lead to at least some degree of denaturation and may also affect the availability of ligand binding sites. On the other hand, the avidin can be oriented on the planar substrate by first adsorbing a layer of biotinylated bovine serum albumin (BSA) (see FIG. 7B). BSA is a soft protein that easily spreads on a planar substrate to form a uniform coating. Once adsorbed, it should prevent the non-specific adsorption of most other proteins with the surface. However, because the BSA will be biotinylated, it allows avidin to bind specifically and thus orient at the surface. This will leave two of the biotin binding sites available for binding with additional biotin species from the aqueous solution.

The significance of performing detection assays with randomly oriented and partially denatured proteins as well as with oriented and native protein molecules is straightforward. These assays can be used as benchmarks for comparison with the homogeneous system. The equilibrium dissociation constant obtained for the oriented heterogeneous system should approach the value obtained in bulk solution. On the other hand, there may be less fluorescence intensity increase per avidin since the binding sites on the lower side of the macromolecule are presumably unavailable. Moreover, the change in fluorescent intensity with the randomly oriented system will be significantly lower as any number of binding sites could be denatured by the adsorption process. This would be in addition to any changes that would result from making these binding sites unavailable due to their orientation toward the substrate surface.

The homogeneous vs. heterogeneous assays described above are significant because it is not always advantageous to run the assay in bulk solution. For example, continuous flow assays for detection of biothreats might necessarily need to be run homogeneously.

Calmodulin/$Ca^{2+}$

A third representative system exemplifying the system and methods of the invention is calmodulin/$Ca^{2+}$. Calmodulin is a calcium ion binding protein of molecular weight 16.79 kDa[41] and with a pI value of 3.9-4.3. Calmodulin has numerous physiological functions ranging from muscle contraction and immune response to apoptosis and the regulation of metabolism. The assays with this system differ from those described above for avidin and kinases in several ways. First, the analyte molecule is a positively charged divalent metal cation rather than a small molecule. Second, calmodulin bears a net negative charge near physiological pH. As such, this assay will operate in "turn off" mode at pH 7.4. Also, the data described below were obtained under homogeneous conditions with an attached ortho-TEXAS RED® fluorophore.

Figure 8A:
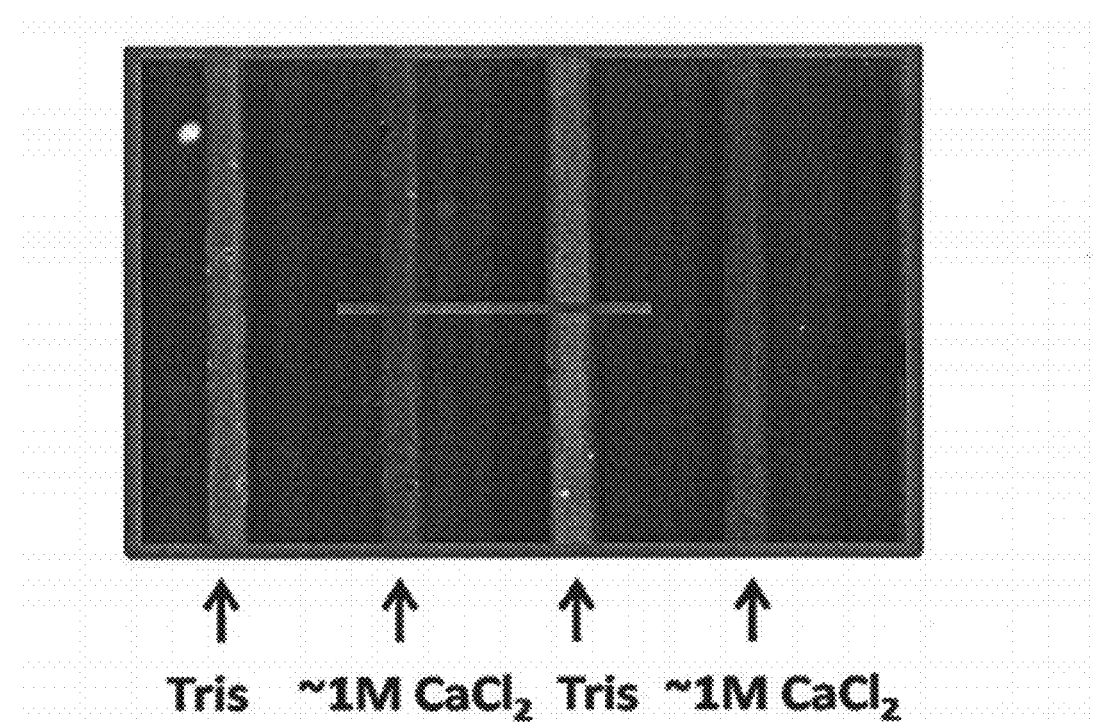
FIG. 8A is a fluorescence image of BSA passivated microfluidic channels (left), each containing 66 μM ortho-TEXAS RED®-conjugated calmodulin in Tris buffer at pH 7.4. The second and fourth channels also contain 1 M calcium chloride.
Figure 8B:
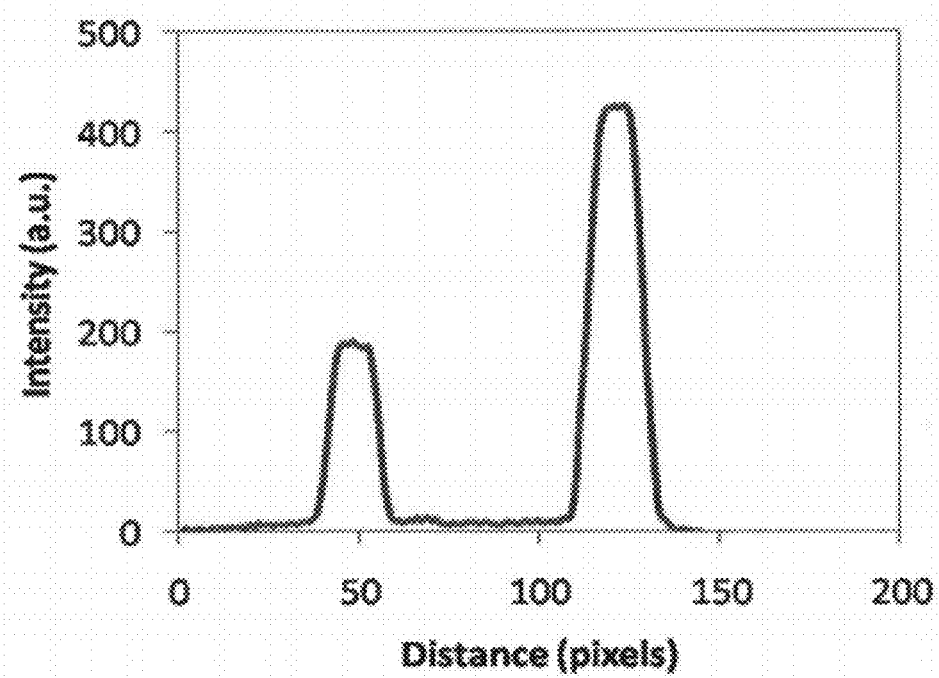
FIG. 8B compares fluorescence emission intensity in the channels (line profile across the system) illustrated in FIG. 8A.

Dye-conjugated calmodulin was placed in microfluidic channels at a concentration of 66 µM with and without 1 M $CaCl_2$ (see FIGS. 8A and 8B). Calmodulin binds to $Ca^{2+}$ with an equilibrium dissociation constant of 14 µM. Therefore, 1 M $CaCl_2$ represents saturation binding conditions. As can be seen from the fluorescence image (FIG. 8A), the assay was run in multiple microfluidic channels that alternated between $CaCl_2$ concentrations of 0 M and 1 M. The pH was maintained at pH 7.4 by 10 mM Tris buffer with the additional 100 mM NaCl. Like the avidin and kinase assays, the signal from the $Ca^{2+}$ studies is strong (i.e., greater than a factor of two attenuation in fluorescence intensity when $Ca^{2+}$ is present).

Protein-Protein Interaction Assays

Figure 9A:
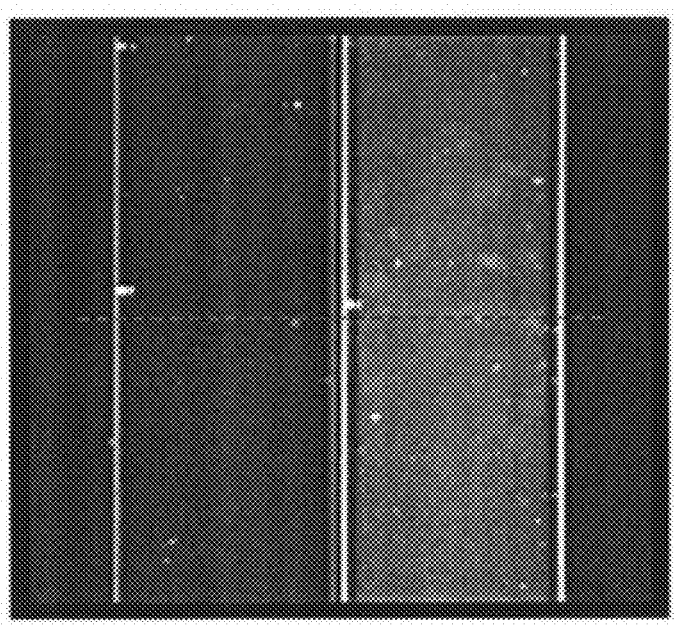
FIG. 9A is a fluorescence image of a two channel assay for the detection of biotinylated BSA by ortho-TEXAS RED® labeled avidin. The left-hand channel contains no BSA and 500 nM biotinylated BSA is present in the right-hand channel.
Figure 9B:
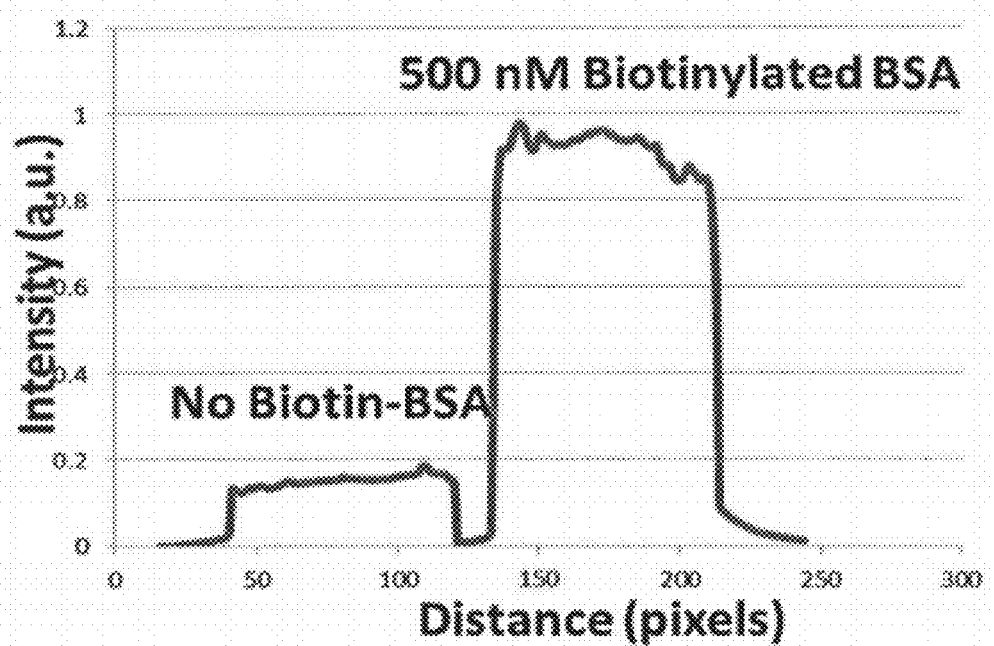
FIG. 9B compares fluorescence emission intensity in the channels (line profile across the system) illustrated in FIG. 9A.

In addition to studying the binding of ions and small molecules with proteins, the method and systems of the invention can be used to explore protein-protein interactions (e.g., the interaction of avidin with biotinylated bovine serum albumin). The fluorescence data are provided in FIGS. 9A and 9B and are similar to the data for the simple biotin-avidin system described above. The data were taken by introducing 3 μM ortho-TEXAS RED® succinimidyl ester labeled avidin into two parallel microfluidic channels at 150 mM NaCl and 10 mM PBS at pH 7.0. In addition, 500 nM biotinylated BSA was added to the right-hand channel, but not the left. As can be seen from the fluorescence line scan (FIG. 9B), the signal in the right-hand channel was approximately eight times brighter than in the left. As such, this is a "turn-on" sensor, which is expected since BSA bears a net negative charge at pH 7.0 as it has an isoelectric point of 4.7. Control experiments with para-TEXAS RED® under identical conditions showed no difference between the two channels. The data are significantly different from simple biotin measurements because they were made more than a full pH unit lower. Indeed, it is not expected that optimized conditions would be the same for biotinylated BSA and biotin. That is because the charge and size of the analytes are very different. Most importantly, these results indicate that pH modulation assays could be used to monitor protein-protein interactions.

Local site pH modulation assays are useful for monitoring ligand-receptor binding to proteins as well as protein-protein interactions.

PNA/DNA Binding Assay for the Detection of $Hg^{2+}$

The methods and system of the present invention can be used to characterize the interaction of nucleic acid strands and the formation of the double helix structure, which include large changes in the local electric fields because of the high charge coming from the DNA backbone. In one embodiment, the method employs a protein nucleic acid (PNA) as the complementary strand because PNA-based polymers are net neutral (see FIG. 10).

Figure 10:
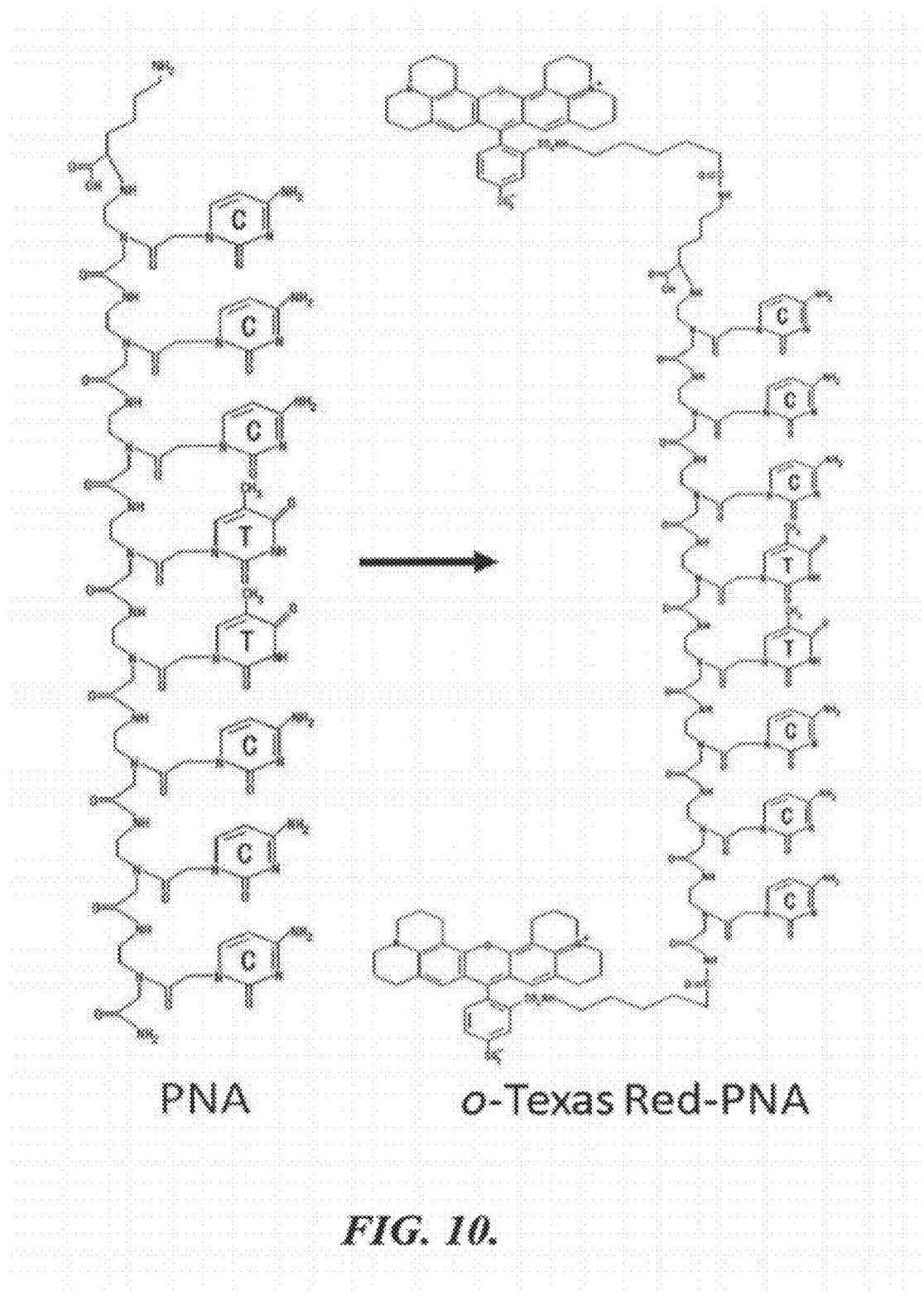
FIG. 10 is a schematic illustration of a PNA strand sequence CCCTTCCC (SEQ ID NO: 2) and a fluorescent conjugate of the strand labeled on both ends with ortho-TEXAS RED®.

PNAs consist of a peptide backbone (polyglycine) instead of the sugar phosphate backbones that occur in DNA and RNA. Any of the four natural nucleic acids can be attached at the nitrogen to form N-(2-amino-ethyl)-glycine units. These molecules can be readily labeled at both ends by a succinimidyl ester of ortho-TEXAS RED® (FIG. 10). Therefore, the binding of DNA will cause the sensor to work in "turn-on" mode when working near physiological pH.

In a first assay, the eight base long PNA strand, CCCT-TCCC (SEQ ID NO: 2), can be demonstrated to detect the binding of the complementary DNA strand, GGGAAGGG (SEQ ID NO: 1).

Figure 11:
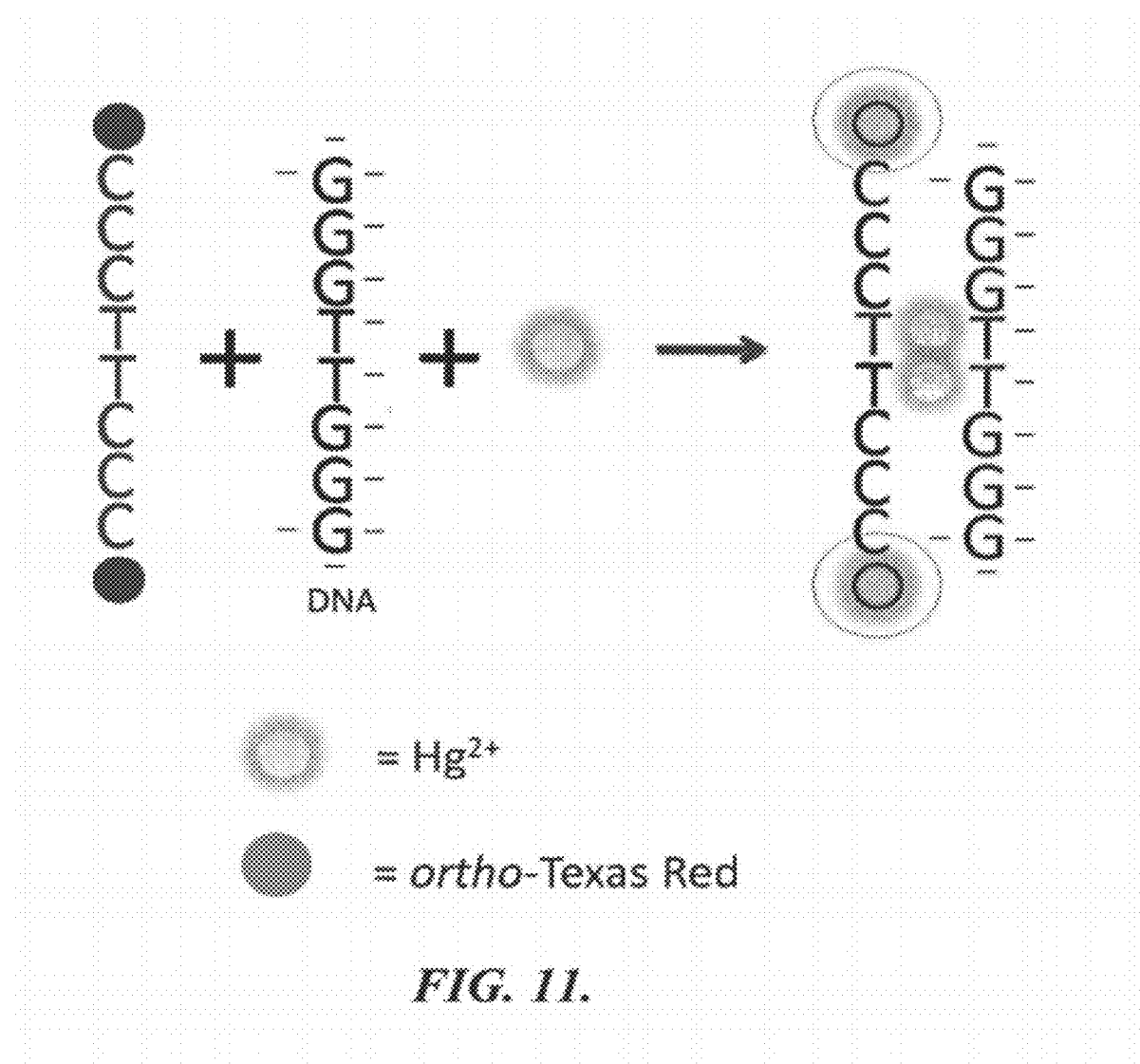
FIG. 11 is a schematic illustration of a PNA-DNA binding platform for the detection of $Hg^{2+}$. The strands (CCCTTCCC (SEQ ID NO: 2) and GGGTTGGG (SEQ ID NO: 1) hybridize when $Hg^{2+}$ is added to the system as that event will allow the two T-T bases to coordinate.

In one embodiment, the invention provides a PNA-DNA assay effective to detect a $Hg^{2+}$ sensor that functions in aqueous solution. Fabrication of $Hg^{2+}$ detection assays that work in pure aqueous solutions have typically been difficult to create. Most assays either require at least some organic solvent or are quite cumbersome. The assay of the present invention takes advantage of the known binding of $Hg^{2+}$ ions at T-T mismatches (FIG. 11). The same PNA strand is employed as shown in FIG. 10, CCCTTCC (SEQ ID NO: 2). However, the DNA strand used in this assay is GGGTTGGG (SEQ ID NO: 1). In the absence of $Hg^{2+}$, the binding between these two strands is quite weak because of the presence of the double mismatch in the center. However, the binding should markedly improve as $Hg^{2+}$ is added to the system.

The response of this assay is different from the protein-ligand binding systems described above. In those situations, negatively charged analytes typically give rise to "turn-on" sensors, while positively charged analytes work as "turn-off" sensors. In this case, despite the fact that the metal ion has a positive two charge, the assay works in "turn on" mode. This occurs for two reasons. First, the charge on the DNA is much greater than that of the $Hg^{2+}$ ions (−12 vs. +2). Second, the highly negatively charged 3' and 5' prime ends of the DNA strand should come into closest proximity with the dye label on the PNA upon complementary binding.

Homogeneous Assays and Readout by a Fluorimeter or Plate Reader

The methods of the invention demonstrate that pH modulation assays can be run homogeneously. Therefore, the assays can be incorporated into simple plate readers, 96 well plate assay formats, and fluorimeters for detection and binding constant measurements.

Strategy for Labeling Proteins and Choice of Fluorophores

The pH modulation assay of the invention is compatible with various fluorophores. Representative red-emitting pH-sensitive dyes (e.g., PHRODO®, ortho-TEXAS RED®) have been demonstrated as useful in the systems and methods of the invention. Other pH-sensitive dyes are also suitable. Assays using fluorescein or coumarin, and their derivatives, can be turned on and off as the pH is varied. However, fluorescein or coumarin dyes are more readily photobleached and are therefore more difficult to employ in practice for quantitative assays. There are advantages to using different dyes for different purposes. For example, in one embodiment, multiple colors (i.e., dyes) can be used to simultaneously investigate multiple analytes in a system. It can also be useful to use dye molecules that operate under different pH conditions. In this sense, the PHRODO® dye is quite useful as it has an apparent $pK_A$ which is significantly lower than that of ortho-TEXAS RED®. As shown in FIG. 4, the titration point for this dye on protein kinase A is pH 5.8. Based upon data for avidin and calmodulin, the titration point for ortho-TEXAS RED® should be a couple of pH units higher on the same protein.

Preparation of Ortho-TEXAS RED® Succinimidyl Ester

Figure 12:
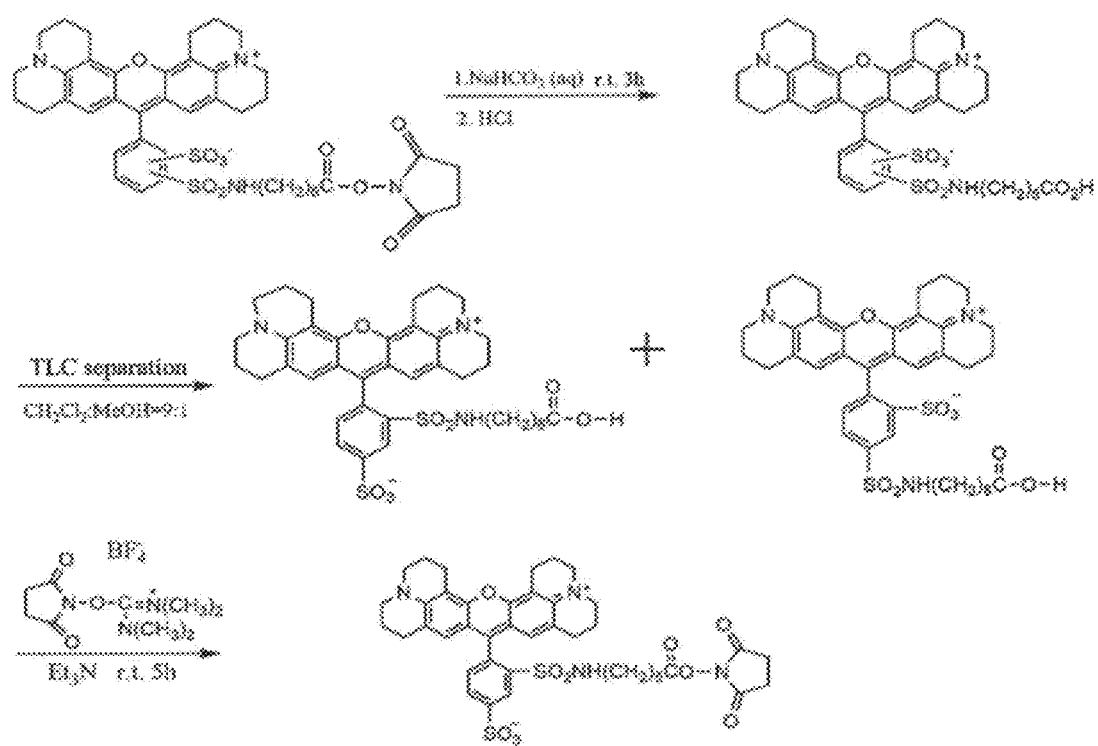
FIG. 12 is a schematic illustration of the preparation of ortho-TEXAS RED® succinimidyl ester.

The preparation of ortho-TEXAS RED® succinimidyl ester from a mixture of ortho- and para-TEXAS RED® succinimidyl ester, by hydrolysis, isomer separation, and reactivation of the ortho-TEXAS RED® succinimidyl ester is illustrated schematically in FIG. 12. Specifically, the ortho- and para-TEXAS RED® succinimidyl ester mixture was first hydrolyzed in 0.01 M $NaHCO_3$ in aqueous solution for 3 hr at room temperature, which converted the succinimidyl ester to the corresponding and less reactive acid mixture. The solution pH is then lowered to 7.0 by adding sufficient HCl. Next, the isomers are extracted into methylene chloride. This organic solution is allowed to partially evaporate under vacuum to concentrate the dyes. Then, the isomeric mixture is spotted onto a thin layer chromatography plate (TLC) for separation. The solvent used to separate the ortho and para isomers is a 9:1 mixture by volume of methylene chloride and methanol. The ortho isomer moves slower under these circumstances and this band is removed and dissolved into the $CH_2Cl_2$ and $CH_3OH$ solvent mixture again. The solvent was allowed to evaporate and the ortho dye was re-dissolved in pure methylene chloride. The dye was reactivated to the succinimidyl ester by adding a 1.2 molar equivalent of N,N,N',N'-tetramethyl-O-(N-succinimidyl) uranium tetrafluoroborate and a 1.5 molar equivalent of triethylamine to the solution. This mixture was stirred at room temperature for 5 hours to yield back the ortho-TEXAS RED® succinimidyl ester. The ortho dye was then partitioned into pure water and the triethylamine was evaporated away. At this point, isomerically pure aqueous dye could be directly conjugated to a target protein molecule.

TERMINOLOGY

As used herein, an "ortho-sulforhodamine 101-conjugate" refers to a compound comprising ortho-sulforhodamine 101 conjugated to a moiety:

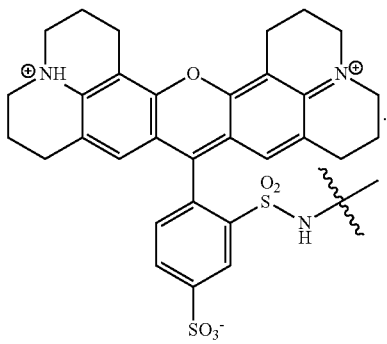

For example, an ortho-sulforhodamine 101-conjugate may be attached, directly or indirectly (through a linker, such as a polymer, such that the linker does not interfere with fluorescence measurement), to a ligand, receptor, polymer, lipid, or surface coating (e.g., metals such as Au via a thiol, or polymer bead via a linker). As used herein, "ortho-TEXAS RED®-conjugate" and "ortho-sulforhodamine 101-conjugate" are used interchangeably.

As used herein, a "para-sulforhodamine 101-conjugate" refers to a compound comprising para-sulforhodamine 101 conjugated to a moiety:

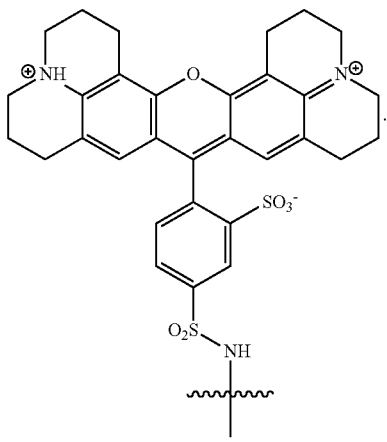

For example, a para-sulforhodamine 101-conjugate may be attached, directly or indirectly (through a linker, such as a polymer, such that the linker does not interfere with fluorescence measurement), to a ligand, receptor, polymer, lipid, or surface coating (e.g., metals such as Au via a thiol, or polymer bead via a linker). As used herein, "para-Texas Red-conjugate" and "para-sulforhodamine 101-conjugate" are used interchangeably.

As used herein, a "PHRODO®-conjugate" refers to a compound comprising PHRODO® conjugated to a moiety (e.g., ligand, receptor, substrate). A reactive form of PHRODO® suitable for conjugation is commercially available from Life Technologies, Invitrogen (e.g., PHRODO® succinimidyl ester is catalog number P36600). The apparent $pK_A$ value of PHRODO® is typically shifted to more acidic pH values than TEXAS RED® under similar conditions. A PHRODO®-conjugate may be attached, directly or indirectly (through a linker, such as a polymer, such that the linker does not interfere with fluorescence measurement), to a ligand, receptor, polymer, lipid, or surface coating (e.g., metals such as gold via a thiol, or polymer bead via a linker). PHRODO® and PHRODO®-conjugates may be employed in embodiments as described in WO/US2010/080640, incorporated herein by reference.

As used herein, "ligand" refers to a moiety that is capable of binding to a receptor. A ligand and a receptor have a binding constant that is sufficiently strong to allow detection of binding by an assay method that is appropriate for detection of a ligand binding to a receptor (e.g., a second messenger assay to detect an increase or decrease in the production of a second messenger in response to ligand binding to the receptor; a binding assay to measure protein-ligand binding; an immunoassay to measure antibody-antigen interactions; a method as described herein; or other in vitro assays). A ligand and receptor specifically bind to each other (e.g., via covalent or hydrogen bonding). In certain embodiments, the $K_d$ of a receptor-ligand interaction is, at most 100 mM. In certain embodiments, the $K_d$ is at most about, at least about, or about 100 mM, 75 mM, 50 mM, 25 mM, 10 mM, 1 mM, 750 μM, 500 μM, 250 μM, 100 μM, 10 μM, 1 μM, 750 nM, 500 nM, 250 nM, 100 nM, 10 nM, 1 nM, 750 pM, 500 pM, 250 pM, 100 pM, 50 pM, 20 pM, 10 pM, 1 pM, 750 fM, 500 fM, 250 fM, 100 fM, 50 fM, 10 fM, 5 fM, 2 fM, 1 fM, or lower. Suitable ligands include those known in the art, including both naturally occurring and artificially prepared. A ligand may be, for example, an ion (e.g., $Hg^{2+}$), drug, antibiotic, nucleotide, antibody, antigen, hapten, hormone, steroid, enzyme, neurotransmitter, peptide, peptidomimetic, protein, nucleic acid, protein nucleic acid, toxin, agonist, or antagonist, where these classes are not necessarily mutually exclusive. A ligand may have a net positive charge, a net negative charge, or may be neutral. A ligand may be a small organic molecule (e.g., having a molecular weight of less than 1,000 g/mol). A variety of ligands are described in, e.g., The Merck Index: An Encyclopedia of Chemicals, Drugs, and Biologicals, 2006. A ligand may be a putative ligand. In some embodiments, the ligand is not a nucleic acid. In some embodiments, if a ligand is immobilized on a substrate, the ligand is presented on the surface of the substrate and not embedded within the substrate (i.e., the ligand is not shielded from the surface).

As used herein, a "receptor" is a molecule that binds a ligand. A receptor may be naturally occurring or artificially prepared. Such molecules include proteins, such as G-protein coupled receptors, enzymes, and antibodies. A receptor may be a cell-surface receptor. A receptor may be DNA, for example, as certain ligands bind to DNA (e.g., an intercalator or a protein nucleic acid). Vancomycin is another non-peptide receptor, where D-Ala-D-Ala is a ligand. A receptor may have a net positive charge, a net negative charge, or may be neutral. A receptor may be presented on the surface of an entity, such as a bacteria or a virus. A receptor may be a putative receptor. In some embodiments, a receptor does not comprise a surface of a substrate. In some embodiments, if a receptor is immobilized on a substrate, the receptor is presented on the surface of the substrate and not embedded within the substrate (i.e., the receptor is not shielded from the surface).

By "substantially free of para-sulforhodamine 101" or "substantially free of para-sulforhodamine 101-conjugate," it is meant that the para-sulforhodamine 101 or its conjugate is present in an amount that is less than about 5% of that of its isomer, ortho-sulforhodamine 101 or its conjugate. In certain embodiments, it is present in an amount of at most 5%, 4.5%, 4%, 3.5%, 3%, 2.5%, 2%, 1.5%, 1%, 0.5%, or less. Any embodiment herein may be substantially free of para-sulforhodamine 101 or its conjugate.

By "substantially free of ortho-sulforhodamine 101" or "substantially free of ortho-sulforhodamine 101-conjugate,"

it is meant that the ortho-sulforhodamine 101 or its conjugate is present in an amount that is less than about 5% of that of its isomer, para-sulforhodamine 101 or its conjugate. In certain embodiments, it is present in an amount of at most 5%, 4.5%, 4%, 3.5%, 3%, 2.5%, 2%, 1.5%, 1%, 0.5%, or less. Any embodiment herein may be substantially free of ortho-sulforhodamine 101 or its conjugate.

As used herein, "optically separated" refers to the fact that to detect the ortho and para isomers of sulforhodamine 101 optically, they have to be spatially separated. This means that they are bound to a substrate in two separate location. Those locations should be separated beyond the diffraction limit (about 500 nm) so that they can be easily discerned. In practice, for example, if the location size is 5 µm×5 µm, separation by a 5 µm spacer is suitable. These distances can be judged by optical microscopy using a standard CCD camera for detection, as is known in the art. Thus, optically separated fluorophores are physically separated to a distance where they can be measured separately by microscopy and separated to a physical distance beyond the diffraction limit.

A substrate, such as a bead, that comprises a receptor, ligand, fluorophore, or any other agent described herein may refer to such an agent that is immobilized onto or into, covalently bound to, or non-covalently bound to the surface of the substrate. When an agent is immobilized, it is typically immobilized in a way that presents the agent on the surface of the substrate (that is, the external surface of the substrate). A linker may join the agent to the substrate, wherein the linker is covalently bound to the agent and to the substrate. Any linker known in the art may be employed provided it does not prevent the receptor from binding to the ligand and does not prevent fluorescence measurement. A pH-sensitive fluorophore may be immobilized to the same surface of a substrate as either a ligand or a receptor. In some embodiments, if a fluorophore is immobilized on a substrate, the fluorophore is presented on the surface of the substrate and not embedded within the substrate (i.e., the fluorophore is not shielded from the surface).

As used herein, "lipid" refers to a straight-chain hydrocarbon radical having 5 carbons or higher, wherein the radical may comprise single, double, and/or triple bonds. In certain embodiments, the straight-chain hydrocarbon radical has between 5 and 45 carbon atoms. Non-limiting examples of lipids include —$C_5H_{11}$, —$C_{11}H_{23}$, —$C_{15}H_{31}$, —$C_{19}H_{39}$ and —$C_{17}H_{31}$.

In some embodiments, an assay may be optimized to achieve the lowest possible limit of detection. Both the ligand density and the concentration of pH-sensitive fluorophore molecules may be modulated for this purpose. The limit of detection (LOD) for some assay embodiments may be established in terms of the lowest concentration of analyte protein which may be detected and/or the lowest number density of proteins which can be reliably detected on the substrate surface. In some embodiments, a detection limit of 10 proteins/$\mu m^2$ at the surface or less may be achieved. LOD values may be tested with a variety of binding systems including antibody/antigen, concanavalin A/mannose, and $GM_1$/cholera toxin.

The use of the term "or" in the claims is used to mean "and/or" unless explicitly indicated to refer to alternatives only or the alternatives are mutually exclusive. It is specifically contemplated that any listing of items using the term "or" means that any of those listed items may also be specifically excluded from the related embodiment.

Throughout this application, the term "about" is used to indicate that a value includes the standard deviation of error for the device or method being employed to determine the value.

As used herein the specification, "a" or "an" may mean one or more, unless clearly indicated otherwise. As used herein in the claims, when used in conjunction with the word "comprising," the words "a" or "an" may mean one or more than one.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has," or "includes" one or more steps is not limited to possessing only those one or more steps and also covers other unlisted steps.

As an alternative to or in addition to "comprising," any embodiment herein may recite "consisting of." The transitional phrase "consisting of" excludes any element, step, or ingredient not specified in the claim.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of detecting binding between a first molecule and a second molecule, comprising:
    obtaining a first fluorescence measurement of a pH-sensitive fluorophore-labeled molecule, wherein the pH-sensitive fluorophore-labeled molecule is an ortho-sulforhodamine 101-labeled molecule;
    contacting the pH-sensitive fluorophore-labeled molecule with a second molecule, wherein the second molecule is a non-fluorescently-labeled molecule; and
    obtaining a second fluorescence measurement of the pH-sensitive fluorophore-labeled molecule, wherein a change in fluorescence between the first and second measurements is indicative of binding of the pH-sensitive fluorophore-labeled molecule to the second molecule.

2. The method of claim 1, wherein the pH-sensitive fluorophore-labeled molecule and the second molecule are in solution.

3. The method of claim 1, wherein the pH-sensitive fluorophore-labeled molecule or the second molecule are immobilized on a substrate.

4. The method of claim 1, wherein the pH-sensitive fluorophore-labeled molecule is a pH-sensitive fluorophore-labeled receptor.

5. The method of claim 4, wherein the second molecule is a ligand.

6. The method of claim 1, wherein the pH-sensitive fluorophore-labeled molecule is a pH-sensitive fluorophore-labeled ligand.

7. The method of claim 6, wherein the second molecule is a receptor.

8. The method of claim 1, wherein the pH-sensitive fluorophore-labeled molecule is a pH-sensitive fluorophore-labeled PNA.

9. The method of claim 8, wherein the second molecule is a DNA.

10. The method of claim 1, wherein the pH-sensitive fluorophore-labeled molecule is a pH-sensitive fluorophore-labeled DNA.

11. The method of claim 10, wherein the second molecule is a PNA.

12. The method of claim 1, wherein the pH-sensitive fluorophore-labeled molecule is an ortho-sulforhodamine 101-labeled molecule that is substantially free of para-sulforhodamine 101-labeled molecule.

13. A method of detecting binding between a protein nucleic acid (PNA) and a deoxyribonucleic acid (DNA), comprising:
    obtaining a first fluorescence measurement of a first solution comprising a PNA;
    introducing a second solution comprising a DNA to the first solution to form a third solution,
    wherein the PNA or the DNA, but not both, is labeled with a pH-sensitive fluorophore, wherein the pH-sensitive fluorophore is ortho-sulforhodamine 101; and
    obtaining a second fluorescence measurement of the third solution, wherein a change in fluorescence between the first and second fluorescence measurements is indicative of binding of the PNA and the DNA to form a PNA/DNA complex.

14. The method of claim 13, wherein the PNA is labeled with a pH-sensitive fluorophore.

15. The method of claim 13, wherein the PNA or the DNA labeled with the pH-sensitive fluorophore is substantially free of PNA or the DNA labeled with para-sulforhodamine 101.

16. The method of claim 15, wherein the method further comprises employing either para-sulforhodamine 101-labeled PNA or para-sulforhodamine 101-labeled DNA as a reference.

17. The method of claim 13 further comprising measuring a melting curve of the PNA/DNA complex.

18. The method of claim 13, wherein the third solution has a pH ranging within about 1 to about 2 pH units of the pKa of the pH-sensitive fluorophore.

19. The method of claim 13, wherein each solution is an aqueous solution that does not comprise organic solvent.

20. The method of claim 13 further comprising adding $Hg^{2+}$ to the third solution to obtain a fourth solution; and obtaining a third fluorescence measurement of the fourth solution, wherein a change in fluorescence between the second and third fluorescence measurements is indicative of the binding of $Hg^{2+}$ to the PNA/DNA complex.

21. The method of claim 20, wherein each solution is an aqueous solution that does not comprise organic solvent.

22. A method of detecting binding between a first molecule and a second molecule, comprising:
    obtaining a first fluorescence measurement of a pH-sensitive fluorophore-labeled substrate and a first non-fluorescently-labeled molecule, wherein the pH-sensitive fluorophore-labeled substrate is an ortho-sulforhodamine 101-labeled substrate;
    contacting the pH-sensitive fluorophore-labeled substrate with a second non-fluorescently-labeled molecule in the presence of the first molecule; and
    obtaining a second fluorescence measurement of the pH-sensitive fluorophore-labeled substrate, wherein a change in fluorescence between the first and second measurements is indicative of binding of the first molecule to the second molecule.

23. The method of claim 22, wherein the first molecule is a receptor and the second molecule is a ligand.

24. The method of claim 22, wherein the first molecule is a ligand and the second molecule is a receptor.

25. The method of claim 22, wherein the first molecule is a PNA and the second molecule is a DNA.

26. The method of claim 22, wherein the first molecule is a DNA and the second molecule is a PNA.

* * * * *

SEQUENCE LISTING

<160> NUMBER OF SEQ ID NOS: 2

<210> SEQ ID NO 1
<211> LENGTH: 8
<212> TYPE: DNA
<213> ORGANISM: Artificial Sequence
<220> FEATURE:
<223> OTHER INFORMATION: Synthetic

<400> SEQUENCE: 1 gggaaggg                                                                 8

<210> SEQ ID NO 2
<211> LENGTH: 8
<212> TYPE: DNA
<213> ORGANISM: Artificial Sequence
<220> FEATURE:

-continued

```
<223> OTHER INFORMATION: Synthetic

<400> SEQUENCE: 2 cccttccc                                                                8
```